United States Patent [19]
Ben-Sasson

[11] Patent Number: 6,121,236
[45] Date of Patent: Sep. 19, 2000

[54] MULTIVALENT LIGANDS WHICH MODULATE ANGIOGENESIS

[75] Inventor: Shmuel A. Ben-Sasson, Jerusalem, Israel

[73] Assignee: The Children's Medical Center Corporation, Boston, Mass.

[21] Appl. No.: 09/046,985

[22] Filed: Mar. 24, 1998

[51] Int. Cl.$^7$ .............................. A61K 38/00; C07K 5/00; C07K 7/00; C07K 17/00

[52] U.S. Cl. ................................ 514/12; 514/13; 514/14; 514/15; 530/324; 530/325; 530/326; 530/327; 530/328

[58] Field of Search .................................. 514/12, 15, 14, 514/13; 530/324, 328, 327, 326, 325

[56] References Cited

U.S. PATENT DOCUMENTS

| | | | |
|---|---|---|---|
| 5,399,667 | 3/1995 | Frazier et al. | 530/327 |
| 5,643,783 | 7/1997 | Olsen et al. | 435/325 |

FOREIGN PATENT DOCUMENTS

| | | |
|---|---|---|
| WO 95/05191 | 2/1995 | WIPO . |
| WO 96/17059 | 1/1996 | WIPO . |

OTHER PUBLICATIONS

Good, D.J., et al., "A tumor suppressor–dependent inhibitor of angiogenesis is immunologically and functionally indistinguishable from a fragment of thrombospondin," *Proc. Natl. Acad. Sci. USA*, 87: 6624–6628, (1990).

O'Reilly, M. S. et al., "Endostatin: And Endogenous Inhibitor of Angiogenesis and Tumor Growth," *Cell*, 88:277–285, (1997)

Kosfeld, M. D. et al., "Identification of Active Peptide Sequences in the Carboxyl–terminal Cell Bindin Domain of Human Thrombospondin–1," *The Journal of Biological Chemistry*, 267:16230–16236, (1992).

Kosfeld, M. D. et al., "Identification of a New Cell Adhesion Motif in Two Homologous Peptides from the COOH–terminal Cell Binding Domain of Human Thrombospondin," *The Journal of Biological Chemistry*, 268:8808–8814 (1993).

Tolsma, S.S. et al., "Peptides Drived from Two Separate Domains of the Matrix Protein Thrombospondin–1 Have Anti–Angiogenic Activity," *The Journal of Cell Biology*, 122:497–511 (1993).

Vogel, T. et al., "Modulation of Endothelial Cell Proliferation, Adhesion, and Motility by Recombinant Heparin–Binding Domain and Synthetic Peptides from the Type 1 Repeats of Thrombospondin," *Journal of Cellular Biochemistry* 53:74–84 (1993).

Lin, H. B. et al., "Synthesis, surface, and cell–adhesion properties of polyurethanes containing covalently grafted RGD–peptides," *Journal of Biomedical Materials Research*, 28:329–342, (1994).

Tam, J. P., "Recent advances in multiple antigen peptides," *Journal of Immunological Methods*, 196:17–32, (1996).

Tam, J. P., "Synthetic peptide vaccine design: Synthesis properties of a high–density multiple antigenic peptide system" *Proc. Natl. Acad. Sci. USA*, 85:5409–5413, (1988).

Kim, W. H. et al., "Apoptosis in Human Fibrosarcoma Cells is Induced by a Multimeric Synthetic Tyr–Ile–Gly–Ser–Arg (YIGSR)–containing Polypeptide from Laminin," *Cancer Research*, 54:5005–5010, (1994).

Nomizu, M. et al., "Multimeric Forms of Typr–Ile–Gly–Ser–ARg (YIRGSR) Peptide Enhance the Inhibition of Tumor Growth adn Metastasis," *Cancer Research*, 53:3459–3461, (1994).

Folkman, J., "Angiogenisis in cancer, vascular, rheumatoid and other disease," *Nature Medicine*, 1:27–31 (1995).

Folkman, J., "Clinical Applications of Research on Angiogenesis," *The New England Journal of Medicine*, 333:1757–1763, (1995).

Roberts, D. D., "Regulation of tumor growth and metastasis by thrombospondin–1," *The FASEB Journal*, 10:1183–1191 (1996).

DiPietro, L. A., "Thrombospondin as a regulator of angiogenesis," In: Regulation of Angiogenesis, (eds. Goldberg, I.D., et al., ) pp. 295–314, Birkhäuser Verlag, Basel/Switzerland (1997).

Bornstein, P., "Diversity of Function Is Inherent in Matricellular Proteins: An Appraisal of Thrombospondin 1," *The Journal of Cell Biology*, 130:503–506, (1995).

(List continued on next page.)

*Primary Examiner*—Avis M. Davenport
*Attorney, Agent, or Firm*—Hamilton, Brook, Smith & Reynolds, P.C.

[57] ABSTRACT

Disclosed are novel multivalent ligands represented by the following structural formula:

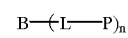

B is a multilinker backbone.

n is an integer from two to about twenty.

Each L is a covalent bond or linking group.

Each P is a peptide having from about 10 to about 30 amino acid residues. At least two of the peptides P are a peptide derivative of an AHR of an angiogenic protein, a hybrid peptide, a peptide derivative of a hybrid peptide or a combination thereof. Each peptide and each linker or covalent bond is independently chosen. The disclosed multivalent ligands can be used to modulate angiogenesis in a mammal.

Also disclosed are novel peptide derivatives of an AHR of an angiogenic protein, novel hybrid peptides, peptide derivatives of the novel hybrid peptides and polypeptide multivalent ligands thereof.

13 Claims, 13 Drawing Sheets

OTHER PUBLICATIONS

Tuszynski, G. P. et al., "The role of thrombospondin–1 in tumor progression and angiogenesis," BioEssays, 18:71–76, (1996).

Qian, X. et al., "Expression of Thrombospondin–1 in Cancer: A Role in Tumor Progression," Proc. Soc. Exp. Biol. Med., 212:199–207, (1996).

Nicosia, R. F. et al., "Matrix–Bound Thrombospondin Promotes Angiogenesis In Vitro," The Journal of Cell Biology, 124:183–193, (1994).

Hsu, S. C. et al., "Inhibition of Angiogenesis in Human Glioblastomas by Chromosome 10 Induction of Thrombospondin–1," Cancer Research 56:5684–5691, (1996).

Iruela–Arispe, M. L. et al., "Thrombospondin–1, an Inhibitor of Angiogenesis, Is Regulated by Progesterone in the Human Endometrium" J. Clin. Invest, 97:403–412, (1996).

Guo, N.H. et al., "Thrombospondin 1 and Type I Repeat Peptides of Thrombospondin 1 Specifically Induce Apoptosis of Endothelial Cells," Cancer Research 57:1735–1743, (1997).

```
                     -5            1             5            10            15            20        25
TSP-1                  R H I G W K D F T A Y R W R L S H R P K T G F I R V V M Y E G K K K M
Endostatin                         Q A R A V G L A G T F R R A F L S S R L Q D L Y S I V R R A D R A A V W
TSP-4                  R N V G W K D K V S Y R W F L Q H R P Q V G Y I R V R F Y E G S E L V
Angiostatin          I S K T M S G L E C Q A W D S Q S P H A H G Y I P S K F P N K N I K K
```

FIGURE 1

SEQ ID NO. 3  Ac-TFRAFLSSRLQTGFIRVVMYEG

SEQ ID NO. 4  Ac-AYRWRLSHRPKDLYSIVRRADG

FIGURE 2

```
                        1              5              10             15          20
SEQ ID NO. 7    Ac- T  F  R  A  F  L  S  S  R  L  Q  D  L  Y  S  I  V  R  R  A  D  G

SEQ ID NO. 8    Ac- A  Y  R  W  R  L  S  H  R  P  K  T  G  F  I  R  V  V  M  Y  E  G

SEQ ID NO. 9    Ac- T  A  Y  R  W  R  L  S  H  R  P  K  D  L  Y  S  I  V  R  R  A  D  R

SEQ ID NO. 10   Ac- A  Y  R  W  R  L  S  H  R  P  K  D  L  Y  S  I  V  R  R  A  D  R

SEQ ID NO. 11      Ac- R  W  R  L  S  H  R  P  K  D  L  Y  S  I  V  R  R  A  D  R

SEQ ID NO. 12   Ac- K  D  F  T  A  Y  R  W  R  L  S  H  R  P  K  D  L  Y  S  I  V  R  R  A  D  R
```

= Tip-19.40
 = (Gly$_4$-Ser)$_3$

MULTIVALENT LIGANDS WHICH MODULATE ANGIOGENESIS

BACKGROUND OF THE INVENTION

Anti-angiogenic therapies are potential treatments for a wide variety of diseases, including cancer, arteriosclerosis, obesity, arthritis, duodenal ulcers, cardiovascular disorders and abnormal ocular neovascularization caused, for example, by diabetes (Folkman, *Nature Medicine* 1:27 (1995) and Folkman, Seminars in Medicine of the Beth Israel Hospital, Boston, *New England Journal of Medicine*, 333:1757 (1995)). Anti-angiogenic therapies are thought to act by inhibiting the formation of new blood vessels.

Pro-angiogenic therapies are potential treatments for promoting wound healing and for stimulating the growth of new blood vessels to by-pass occluded ones. Thus, pro-angiogenic could potentially augment or replace by-pass surgeries and balloon angioplasty (PTCA).

The full potential of anti-angiogenic and pro-angiogenic therapies, together referred to as "angiogenic therapies", has yet to be fully realized. One reason is because of the shortage of agents which modulate neovascularization when administered to a subject. Furthermore, known angiogenic agents suffer from a number of limitations. For example, a number of proteins, including thrombospondin 1 (hereinafter "TSP-1"), h-endostatin (hereinafter "endostatin") and h-angiostatin (hereinafter "angiostatin") are thought to have angiogenic activity. However, the cost of producing protein drugs can be prohibitively high. This concern is of a special relevance when a high dose is required in order to achieve therapeutic efficacy.

The full potential of angiogenic therapies is unlikely to be realized until the problems discussed hereinabove have been overcome.

SUMMARY OF THE INVENTION

This invention is based upon the discovery that angiogenic proteins have a region of about twenty-five amino acids which is substantially conserved among different angiogenic proteins. This region is included in the "angiogenic homology region", also abbreviated as "AHR". It has also been discovered that the angiogenic activity of this class of proteins is attributable, at least in part, to the AHR.

Applicant has also discovered that multivalent ligands comprising peptide derivatives of the AHR of angiogenic proteins modulate angiogenesis in mammals. A multivalent ligand has two or more peptides connected by a covalent bond or linker group to a multilinker backbone. For example, the multivalent ligands Tip-13.40 and Tip-12.40 suppress tumor growth in mice (Example 2). The peptides in Tip-13.40 are represented by SEQ ID NO. 8 and are derivatives of the AHR of TSP-1 (SEQ ID NO.: 1); the peptides in Tip-12.40 are represented by SEQ ID NO.: 7 and are derivatives of the AHR of endostatin (SEQ ID NO.: 2).

A further discovery, reported herein, is that multivalent ligands comprising peptides which are hybrids of the AHR of two different angiogenic proteins also modulate angiogenesis in mammals. For example, the multivalent ligands Tip-14.40, Tip-15.40, Tip-16.40, Tip-18.40 and Tip-19.40 suppress tumor growth in mice (Example 2). The hybrid peptides in Tip-14.40, Tip-15.40, Tip-16.40, Tip-18.40 and Tip-19.40 are represented by SEQ ID NOS.: 3, 4, 10, 11 and 12, respectively, and consist of a subsequence from the AHR of TSP-1 (SEQ ID NO.: 1) and a subsequence from the AHR of endostatin (SEQ ID NO.: 2). In contrast, the multivalent ligand Tip-17.40, which also contains hybrid peptides, stimulates tumor growth in mice. The hybrid peptides in Tip-17.40 are represented by SEQ ID NO.: 9.

Based on the aforementioned discoveries, novel peptides which are peptide derivatives of the AHR of angiogenic peptides are disclosed. Also disclosed are novel peptides which are hybrids of the AHR of angiogenic proteins and peptide derivatives of said hybrids. Novel multivalent ligands which comprise these peptide derivatives and/or hybrid peptides and methods of modulating (inhibiting or stimulating) angiogenesis in a subject with these multivalent ligands are other aspects of the present invention.

One embodiment of the present invention is a multivalent ligand which has angiogenic activity and is represented by Structural Formula (I):

B is a multilinker backbone.

n is an integer from two to about twenty.

Each L is a covalent bond or linking group.

Each P is a peptide having from about 10 to about 30 amino acid residues. At least two of the peptides are peptide derivatives of an AHR of an angiogenic protein, a hybrid peptide or a peptide derivative of a hybrid peptide. Each P and each linker or covalent bond are independently chosen.

Another embodiment of the present invention is a polypeptide multivalent ligand having angiogenic activity. A "polypeptide multivalent ligand" is a tandem repeat polypeptide chain in which two or more peptides P are each separated by a peptide spacer. A polypeptide multivalent ligand is represented by Structural Formula (II):

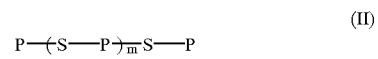

m is an integer from zero to about twenty.

Each P is a peptide having from about ten to about forty amino acid residues. At least two of the peptides are peptide derivatives of an AHR of an angiogenic protein, a hybrid peptide or a peptide derivative of a hybrid peptide.

Each S is a peptide spacer having from about five to about thirty amino acids.

Each peptide P and each peptide spacer are independently chosen. The N-terminus and/or C-terminus of the polypeptide multivalent ligand is optionally substituted, as described below.

Another embodiment of the present invention is a method of modulating (stimulating or inhibiting) angiogenesis in a subject. The method comprises administering a therapeutically effective amount of a multivalent ligand represented by Structural Formula (I) or a polypeptide represented by Structural Formula (II).

The multivalent ligands of the present invention can be used to modulate angiogenesis in a subject. Thus, multivalent ligands which inhibit angiogenesis can be used to treat subjects with cancer and other diseases which respond favorably to drugs which inhibit angiogenesis. Mutlivalent ligands which stimulate angiogenesis can be used to promote wound healing or to stimulate the growth of new blood vessels to bypass, for example, blood vessel occlusions. Multivalent ligands are likely to be less expensive to produce than angiogenic protein drugs. Moreover, multivalent ligands might enable the administration of lower doses in order to achieve therapeutic efficacy, as compared with a univalent peptide chain. In addition, they can have long in vivo lifetimes and good biodistribution when administered orally or parenterally.

BRIEF DESCRIPTION OF THE DRAWINGS

FIG. 1 is a list of sequences illustrating the amino acid sequence for AHR of TSP-1 (SEQ ID NO.: 1), endostatin (SEQ ID NO.: 2), TSP-4 (SEQ ID NO.: 5) and angiostatin (SEQ ID NO.: 6), indicating with underlining the positions where homology is substantially preserved and indicating with numbering the relative position of each amino acid in each amino sequence. Included in FIG. 1 is the core region, in which homology is highly conserved among different angiogenic proteins (positions 1–25), and flanking regions (positions −9 to −1 and 26).

FIG. 2 is a list of sequences illustrating the amino acid sequence of hybrid peptides represented by SEQ ID NO.: 3 and by SEQ ID NO.: 4, which are found in the multivalent ligands Tip-14.40 and Tip-15.40, respectively.

FIG. 3 is a list of sequences illustrating the amino acid sequences for peptide derivatives represented by SEQ ID NO.: 7, SEQ ID NO.: 8, SEQ ID NO.: 9, SEQ ID NO.: 10, SEQ ID NO.: 11 and SEQ ID NO.: 12, which are found in the multivalent ligands Tip-12.40, Tip-13.40, Tip-17.40, Tip-16.40, Tip-18.40 and Tip-19.40, respectively.

FIG. 5 is the consensus sequence for the angiogenic homology region of angiogenic proteins.

DETAILED DESCRIPTION OF THE INVENTION

Figure 4A:
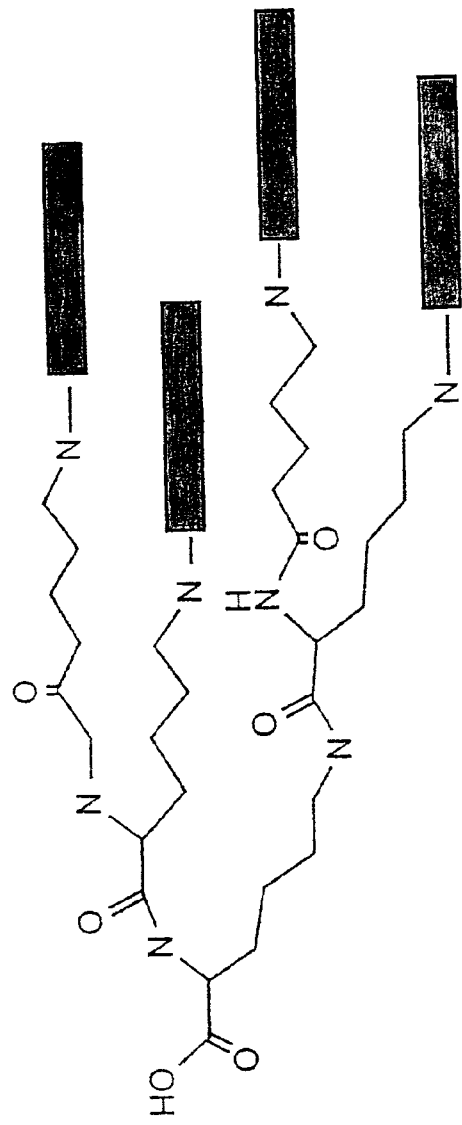
FIGS. 4A–4D are an illustration showing the structures of 4A) a multivalent ligand with an asymmetrical cascading polylysine backbone; 4B) multivalent ligand with a symmetrical cascading polylysine backbone; 4C) multivalent ligand with a pennant polypeptide backbone; and 4D) a multivalent ligand with a pennant polylysine backbone.
Figure 4B:
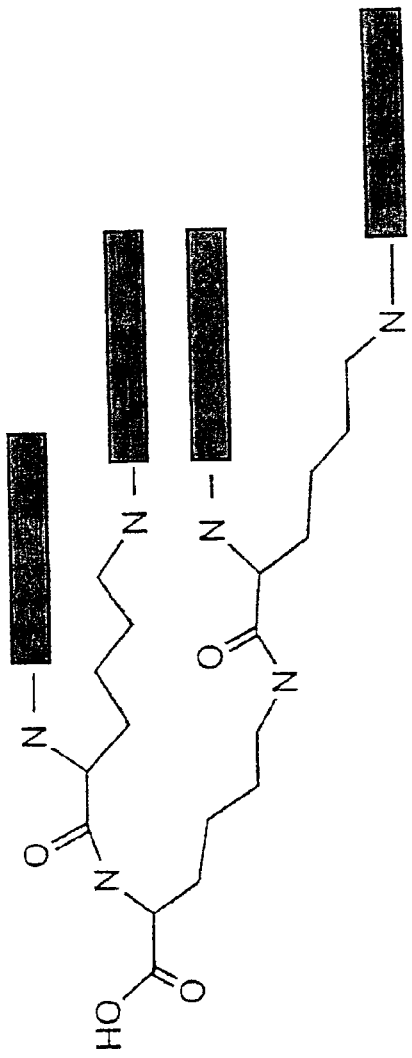
Figure 4C:
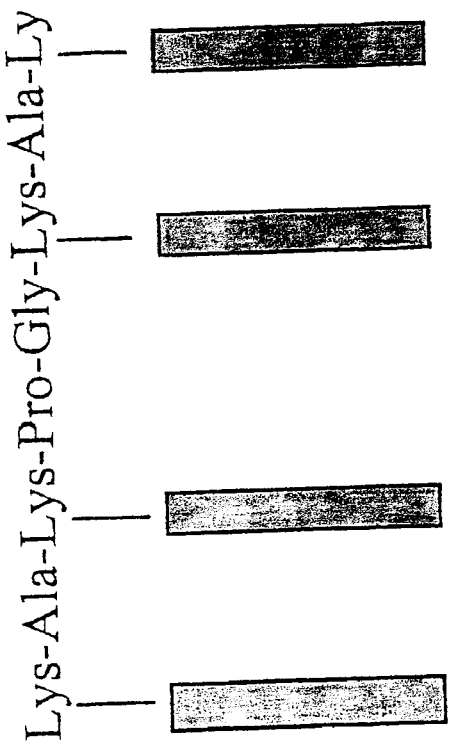
Figure 4D:
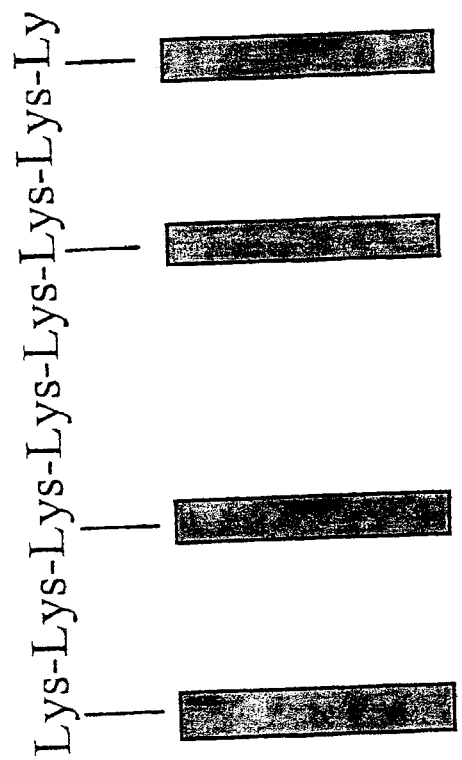
Figure 6:
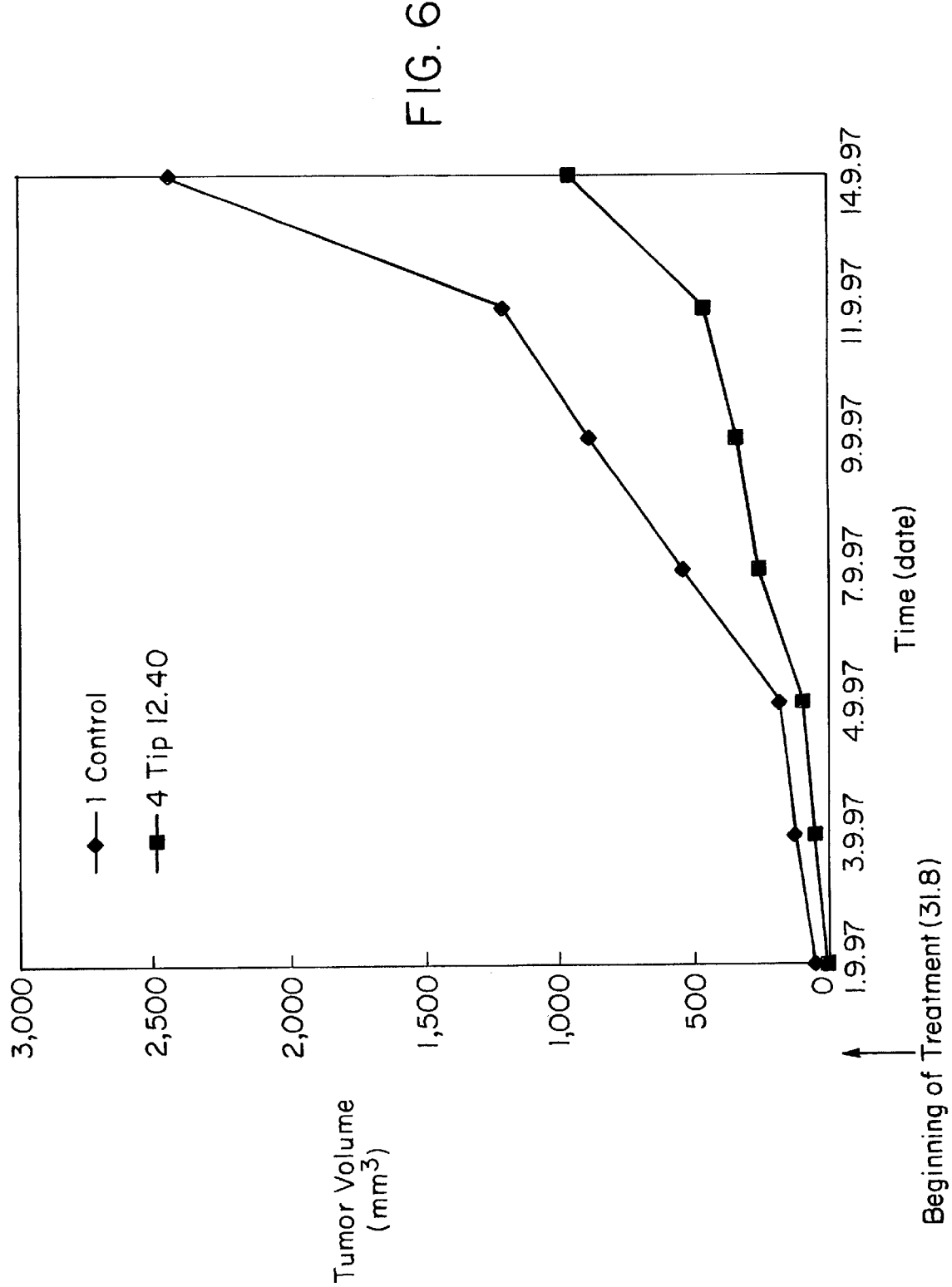
FIG. 6 is a graph showing the volumes of B16 melanoma tumors in mice (measured in mm$^3$) over time (measured in days) after initiation of treatment with the multivalent ligand Tip-12.40. The tumor volumes in Tip-12.40 treated mice are compared with tumor volumes in control mice (vehicle only).
Figure 7:
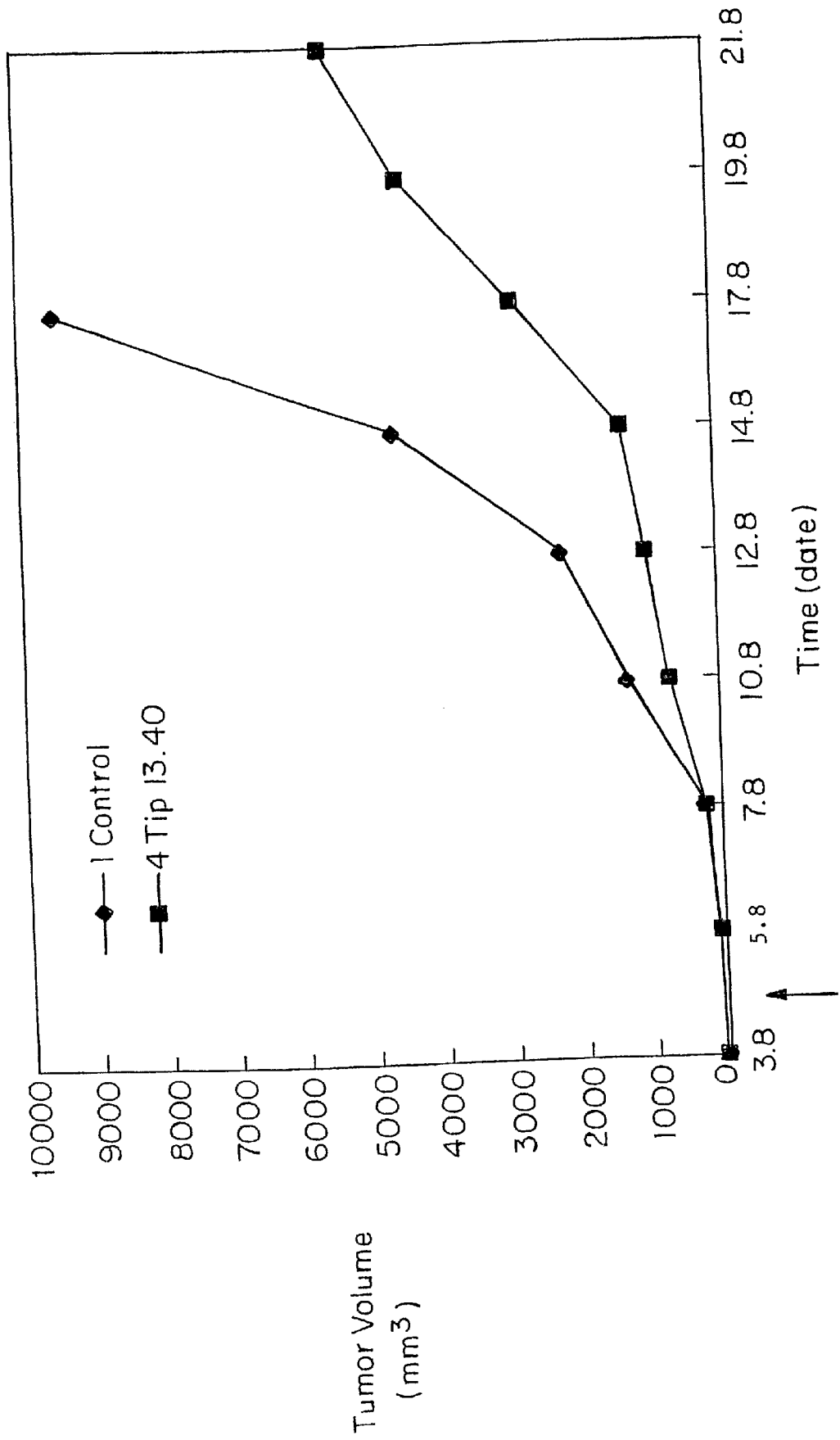
FIG. 7 is a graph showing the volumes of B16 melanoma tumors in mice (measured in mm$^3$) over time (measured in days) after initiation of treatment with the multivalent ligand Tip-13.40. The tumor volumes in Tip-13.40 treated mice are compared with tumor volumes in control mice (vehicle only).
Figure 8:
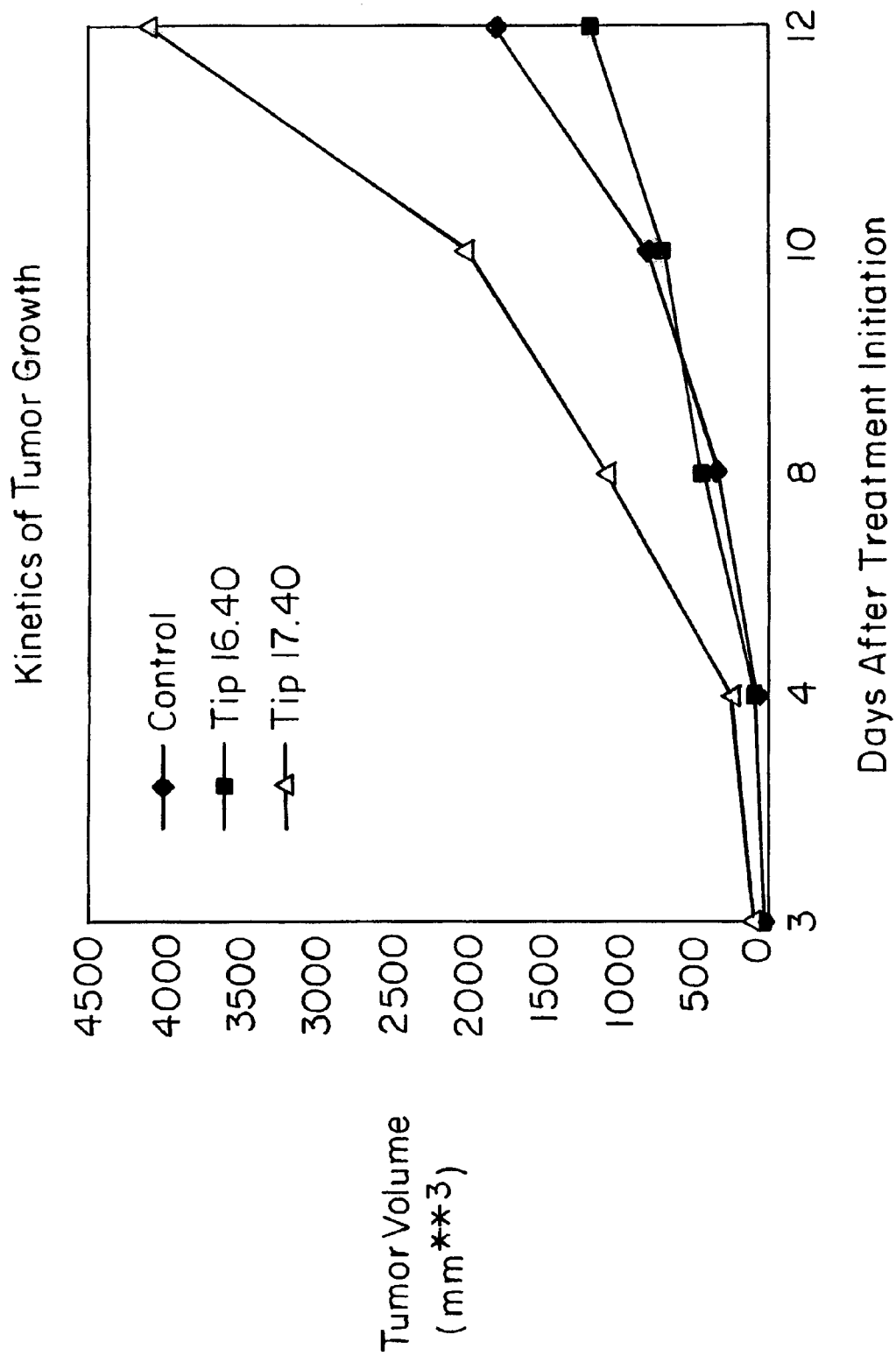
FIG. 8 is a graph showing the volumes of B16 melanoma tumors in mice (measured in mm$^3$) over time (measured in days) after initiation of treatment with the multivalent ligand Tip-16.40 or 17.40. The tumor volumes in Tip-16.40 and Tip-17.40 treated mice are compared with tumor volumes in control mice (vehicle only).
Figure 9:
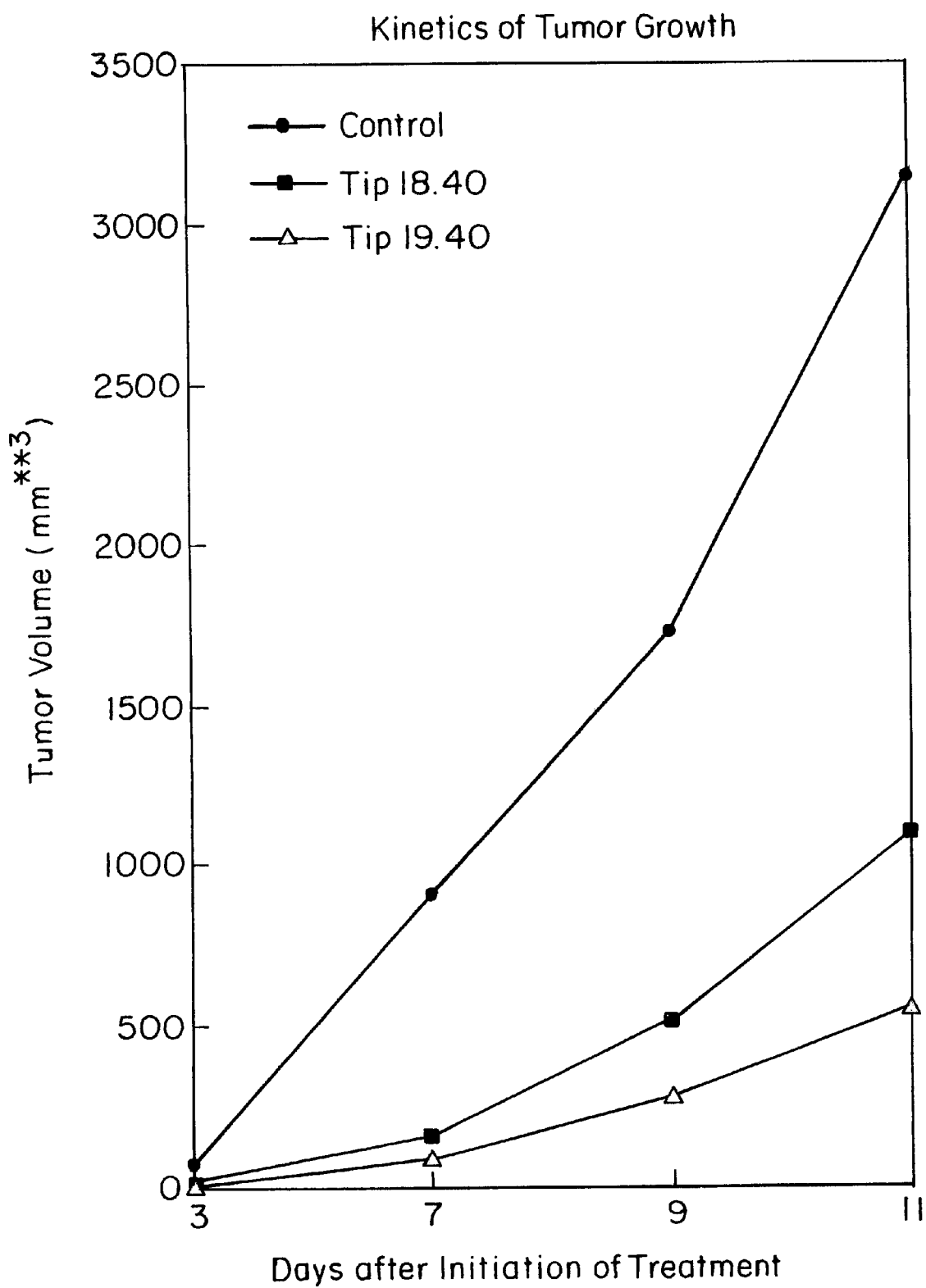
FIG. 9 is a graph showing the volumes of B16 melanoma tumors in mice (measured in mm$^3$) over time (measured in days) after initiation of treatment with the multivalent ligand Tip-18.40 or Tip-19.40. The tumor volumes in Tip-18.40 and Tip-19.40 treated mice are compared with tumor volumes in control mice (vehicle only).

"Angiogenic agents", modulate the development of new blood vessels in mammals. Included within the meaning of the term "angiogenic agents" are molecules which inhibit angiogenesis ("anti-angiogenic agents") and molecules which stimulate or promote angiogenesis ("pro-angiogenic agents"). The development of new blood vessels in mammals is also referred to as "neovascularization". Angiogenic agents include proteins and peptides which modulate angiogenesis, referred to herein as "angiogenic proteins" and "angiogenic peptides", respectively.

Angiogenic agents also include molecules which induce physiological changes in a mammal which are characteristic of angiogenesis modulation. Examples include modulation (promotion or suppression) of tumor growth, tissue repair and tissue remodelling. Peptides which modulate tumor growth when incorporated into multivalent ligands are considered to be angiogenic. Also included within the definition of angiogenic agents are molecules which modulate cellular processes involved in the genesis of blood vessels or the expression of endothelial cell phenotypes. Examples include endothelial cell proliferation, endothelial cell survival, endothelial cell motility, binding to endothelial cells. Agents which modulate cell functions involved in angiogenesis or expression of endothelial cell phenotypes can be identified by in vitro assays which assess, for example, endothelial cell proliferation, endothelial cell survival under restrictive conditions, endothelial cell migration and the binding of white blood cells or platelets to endothelial cells. In vitro assays for identifying angiogenic agents are described in Example 3 of the present application, Tolsma, et al., *J. Cell Biol.* 122:497 (1993) and Vogel et al., *J. Cell. Biochem.* 53:74 (1993). The entire teachings of Tolsma and Vogel are incorporated herein by reference.

Figure 5:
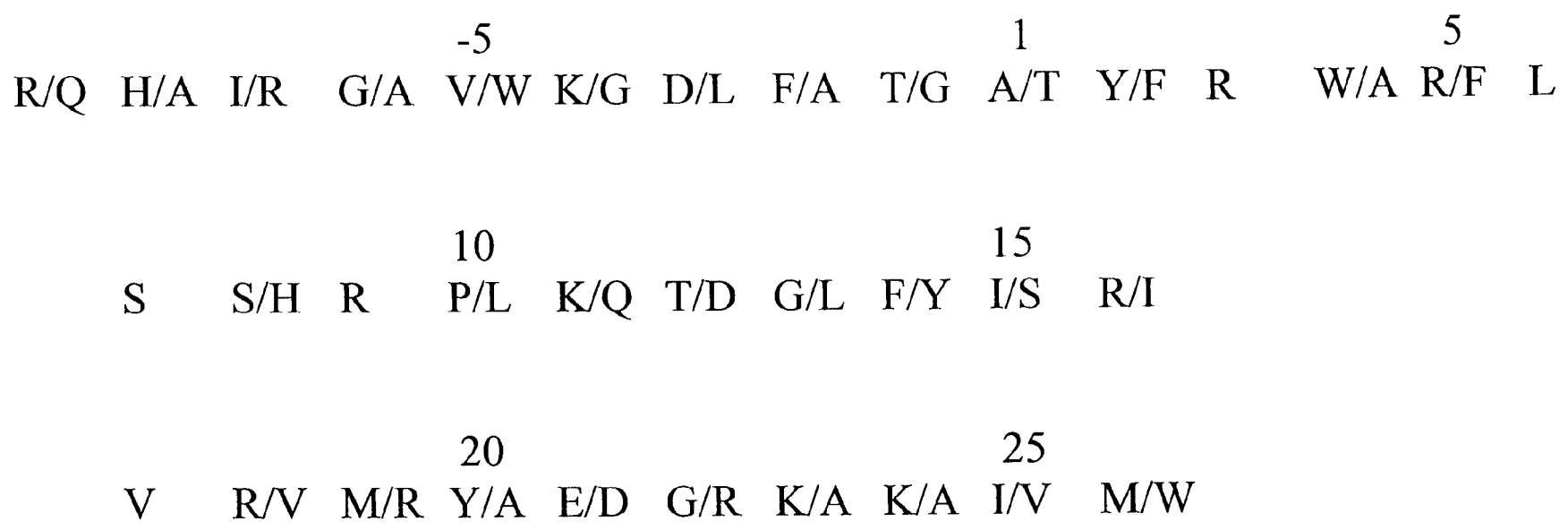

As noted above, Applicant has discovered that angiogenic proteins have an "AHR", which includes a core region in which the amino acid sequence is substantially conserved among several members. Thus, the amino acid sequence of the AHR core of one angiogenic protein is substantially homologous to the AHR core of other angiogenic proteins. An AHR core has between about 10 to about 30 amino acid residues, generally about twenty-five amino acid residues. Once an AHR is identified, its boundaries can optionally be extended to include from about zero to nine flanking amino acids, preferably zero to about four. A consensus sequence for the AHRs of angiogenic proteins is shown in FIG. 5. It has also been found that small peptides having an amino acid sequence corresponding to the amino acid sequence of an AHR can modulate angiogenesis. The location of an AHR is not restricted to any particular part of an angiogenic protein. For example, the AHR of endostatin is located closer to the N-terminus, whereas the AHR of TSP-1 is located near the C-terminus.

"Substantial homology" exists between two amino acid sequences when a sufficient number of amino acid residues at corresponding positions of each amino acid sequence are either identical or structurally related such that a peptide having the first amino acid sequence and a peptide having the second amino acid sequence exhibit similar biological activities. A protein has an AHR when the amino acid sequence of said protein has a subsequence which is substantially homologous to the amino acid sequence of an AHR of an angiogenic protein (or to the consensus sequence for the AHR of angiogenic proteins shown in FIG. 5) such that a peptide having an amino acid sequence corresponding to said subsequence (or said consensus sequence) modulates angiogenesis. Generally, there is substantial homology among the amino acid sequences of two AHRs when at least 30%, and preferably at least 40% of the amino acids in one AHR are identical to or structurally related to the amino acid residues in the other AHR. Substantial homology exists between the amino acid sequence of a peptide and the amino acid sequence of an AHR (or the consensus sequence shown in FIG. 5) when a sufficient number of amino acids at corresponding positions in the amino acid sequence of the peptide and AHR (or consensus sequence) are identical or structurally related such that the peptide is angiogenic. Generally, there is substantial homology between a peptide and an AHR when at least 40%, preferably at least 50% of the amino acids in the peptide are identical to or structurally related to the amino acid residues in the corresponding positions in the AHR, or an angiogenic subsequence thereof. "Structurally related" is defined hereinbelow.

One embodiment of the present invention is a peptide derivative of an AHR of an angiogenic protein. The peptide derivative has angiogenic activity. Examples include peptide derivatives of a peptide represented by SEQ ID NOS.: 2, 5 or 6.

A "peptide derivative of an AHR" includes a peptide having the amino acid sequence of the AHR. A "peptide derivative of an AHR" also includes a peptide having a sequence corresponding to an angiogenic fragment of the AHR. An "angiogenic fragment" is defined to be a peptide whose amino acid sequence corresponds to a subsequence of an AHR, referred to as an "angiogenic subsequence". A subsequence is a sequence of contiguous amino acid residues found within a larger sequence. An angiogenic fragment generally has from about ten to about thirty amino acid residues.

A "peptide derivative" also includes a peptide having a "modified sequence" in which one or more amino acid residues in the original sequence or subsequence have been substituted with a naturally occurring amino acid residue or amino acid residue analog (also referred to as a "modified amino acid residue"). Suitable peptide derivatives have modified sequences which are substantially homologous to the amino acid sequence of an AHR or to an angiogenic subsequence of an AHR. Suitable peptide derivatives also include peptides which are substantially homologous to the consensus sequence for the AHRs of angiogenic proteins, shown in FIG. 5. Peptide derivatives generally have between about ten and about thirty amino acid residues.

In one aspect of the present invention, a peptide derivative has an amino acid sequence corresponding to an angiogenic subsequence of an AHR with between about ten and about fifteen amino acid residues. Zero, one, two or three amino acid residues in the peptide derivative can differ from the amino acid residue(s) in the corresponding position of the subsequence of the AHR. For example, if the subsequence is $[AA_1]$-$[AA_2]$-$AA_3$-$[AA_4]$-$[AA_5]$-$[AA_6]$-$[AA_7]$-$[AA_8]$-$[AA_9]$-$[AA_{10}]$ and one amino acid residue in the sequence of the peptide derivative differs from the amino acid residue in the corresponding position of the subsequence, then the peptide derivative can be $[AA_1']$-$[AA_2]$-$AA_3$-$[AA_4]$-$[AA_5]$-$[AA_6]$-$[AA_7]$-$[AA_8]$-$[AA_9]$-$[AA_{10}]$, $[AA_1]$-$[AA_2']$-$AA_3$-$[AA_4]$-$[AA_5]$-$[AA_6]$-$[AA_7]$-$[AA_8]$-$[AA_9]$-$[AA_{10}]$, $[AA_1]$-$[AA_2]$-$AA_3'$-$[AA_4]$-$[AA_5]$-$[AA_6]$-$[AA_7]$-$[AA_8]$-$[AA_9]$-$[AA_{10}]$, $[AA_1]$-$[AA_2]$-$AA_3$-$[AA_4']$-$[AA_5]$-$[AA_6]$-$[AA_7]$-$[AA_8]$-$[AA_9]$-$[AA_{10}]$, $[AA_1]$-$[AA_2]$-$AA_3$-$[AA_4]$-$[AA_5']$-$[AA_6]$-$[AA_7]$-$[AA_8]$-$[AA_9]$-$[AA_{10}]$, $[AA_1]$-$[AA_2]$-$AA_3$-$[AA_4]$-$[AA_5]$-$[AA_6']$-$[AA_7]$-$[AA_8]$-$[AA_9]$-$[AA_{10}]$, $[AA_1]$-$[AA_2]$-$AA_3$-$[AA_4]$-$[AA_5]$-$[AA_6]$-$[AA_7']$-$[AA_8]$-$[AA_9]$-$[AA_{10}]$, $[AA_1]$-$[AA_2]$-$AA_3$-$[AA_4]$-$[AA_5]$-$[AA_6]$-$[AA_7]$-$[AA_8']$-$[AA_9]$-$[AA_{10}]$, $[AA_1]$-$[AA_2]$-$AA_3$-$[AA_4]$-$[AA_5]$-$[AA_6]$-$[AA_7]$-$[AA_8]$-$[AA_9']$-$[AA_{10}]$ and $[AA_1]$-$[AA_2]$-$AA_3$-$[AA_4]$-$[AA_5]$-$[AA_6]$-$[AA_7]$-$[AA_8]$-$[AA_9]$-$[AA_{10}']$, wherein [AA'] is a naturally occurring or modified amino acid different from [AA].

In another aspect of the present invention, a peptide derivative has an amino acid sequence corresponding to an amino acid sequence or to an angiogenic subsequence of an AHR with between about sixteen and about twenty-eight amino acid residues. Zero, one, two, three or four amino acid residues in the peptide derivative can differ from the amino acid residue(s) in the corresponding position of the sequence or subsequence of the AHR.

An "amino acid residue" is a moiety found within a peptide and is represented by —NH—CHR—CO—, wherein R is the side chain of a naturally occurring amino acid. When referring to a moiety found within a peptide, the terms "amino acid residue" and "amino acid" are used interchangeably in this application. An "amino acid residue analog" includes D or L configurations having the following formula: —NH—CHR—CO—, wherein R is an aliphatic group, a substituted aliphatic group, a benzyl group, a substituted benzyl group, an aromatic group or a substituted aromatic group and wherein R does not correspond to the side chain of a naturally-occurring amino acid.

Suitable substitutions for amino acid residues in the sequence of an AHR or an angiogenic subsequence of an AHR include conservative substitutions which result in peptide derivatives which are angiogenic agents. A conservative substitution is a substitution in which the substituting amino acid (naturally occurring or modified) is structurally related to the amino acid being substituted, i.e., has about the same size and electronic properties as the amino acid being substituted. Thus, the substituting amino acid would have the same or a similar functional group in the side chain as the original amino acid.

A "conservative substitution" also refers to utilizing a substituting amino acid which is identical to the amino acid being substituted except that a functional group in the side chain is functionalized with a suitable protecting group. Suitable protecting groups are described in Green and Wuts, *"Protecting Groups in Organic Synthesis"*, John Wiley and Sons, Chapters 5 and 7, 1991, the teachings of which are incorporated herein by reference. Preferred protecting groups are those which facilitate transport of the peptide through membranes, for example, by reducing the hydrophilicity and increasing the lipophilicity of the peptide, and which can be cleaved, either by hydrolysis or enzymatically (Ditter et al., *J. Pharm. Sci.* 57:783 (1968); Ditter et al., *J. Pharm. Sci.* 57:828 (1968); Ditter et al., *J. Pharm. Sci.* 58:557 (1969); King et al., *Biochemistry* 26:2294 (1987); Lindberg et al., *Drug Metabolism and Disposition* 17:311 (1989); Tunek et al., *Biochem. Pharm.* 37:3867 (1988), Anderson et al., *Arch. Biochem. Biophys.* 239:538 (1985) and Singhal et al., *FASEB J.* 1:220 (1987)). Suitable hydroxyl protecting groups include ester, carbonate and carbamate protecting groups. Suitable amine protecting groups include acyl groups and alkoxy or aryloxy carbonyl groups, as described above for N-terminal protecting groups. Suitable carboxylic acid protecting groups include aliphatic, benzyl and aryl esters esters, as described below for C-terminal protecting groups. In one embodiment, the carboxylic acid group in the side chain of one or more glutamic acid or aspartic acid residues in a peptide of the present invention is protected, preferably as a methyl, ethyl, benzyl or substituted benzyl ester, more preferably as a benzyl ester.

Provided below are groups of naturally occurring and modified amino acids in which each amino acid in a group has similar electronic and steric properties. Thus, a conservative substitution can be made by substituting an amino acid with another amino acid from the same group. It is to be understood that these groups are non-limiting, i.e. that there are additional modified amino acids which could be included in each group.

Group I includes leucine, isoleucine, valine, methionine and modified amino acids having the following side chains: ethyl, n-propyl n-butyl. Preferably, Group I includes leucine, isoleucine, valine and methionine.

Group II includes glycine, alanine, valine and a modified amino acid having an ethyl side chain. Preferably, Group II includes glycine and alanine.

Group III includes phenylalanine, phenylglycine, tyrosine, tryptophan, cyclohexylmethyl, and modified amino residues having substituted benzyl or phenyl side chains. Preferred substituents include one or more of the following: halogen, methyl, ethyl, nitro, —NH$_2$, methoxy, ethoxy and —CN. Preferably, Group III includes phenylalanine, tyrosine and tryptophan.

Group IV includes glutamic acid, aspartic acid, a substituted or unsubstituted aliphatic, aromatic or benzylic ester of glutamic or aspartic acid (e.g., methyl, ethyl, n-propyl iso-propyl, cyclohexyl, benzyl or substituted benzyl), glutamine, asparagine, —CO—NH— alkylated glutamine or asparagine (e.g., methyl, ethyl, n-propyl and iso-propyl) and modified amino acids having the side chain —(CH$_2$)$_3$—COOH, an ester thereof (substituted or unsubstituted aliphatic, aromatic or benzylic ester), an amide thereof and a substituted or unsubstituted N-alkylated amide thereof. Preferably, Group IV includes glutamic acid, aspartic acid, methyl aspartate, ethyl asparatate, benzyl asparate and methyl glutamate, ethyl glutamate and benzyl glutamate, glutamine and asparagine.

Group V includes histidine, lysine, ornithine, arginine, N-nitroarginine, β-cycloarginine, γ-hydroxyarginine, N-amidinocitruline and 2-amino-4-guanidinobutanoic acid, homologs of lysine, homologs of arginine and homologs of ornithine. Preferably, Group V includes histidine, lysine, arginine and ornithine. A homolog of an amino acid includes from 1 to about 3 additional or subtracted methylene units in the side chain.

Group VI includes serine, theronine, cysteine and modified amino acids having C1–C5 straight or branched alkyl side chains substituted with —OH or —SH, for example, —CH$_2$CH$_2$OH, —CH$_2$CH$_2$CH$_2$OH or —CH$_2$CH$_2$OHCH$_3$.

Preferably, Group VI includes serine, cysteine or threonine.

In another aspect, suitable substitutions for amino acid residues in the sequence of an AHR or an angiogenic subsequence of an AHR include "severe" substitutions which result in peptide derivatives which are angiogenic agents. Severe substitutions which result in peptide derivatives that are angiogenic agents are much more likely to be possible in positions which are not highly conserved in the AHRs of angiogenic proteins than at positions which are highly conserved. FIG. 1 shows the amino acid sequence of TSP-1, TSP-4, endostatin and angiostatin and indicates with underlines the positions which are highly conserved.

A "severe substitution" is a substitution in which the substituting amino acid (naturally occurring or modified) has significantly different size and/or electronic properties compared with the amino acid being substituted. Thus, the side chain of the substituting amino acid can be significantly larger (or smaller) than the side chain of the amino acid being substituted and/or can have functional groups with significantly different electronic properties than the amino acid being substituted. Examples of severe substitutions of this type include the substitution of phenylalanine or cycohexylmethyl glycine for alanine, isoleucine for glycine, a D amino acid for the corresponding L amino acid or —NH—CH[(—CH$_2$)$_5$—COOH]—CO— for aspartic acid. Alternatively, a functional group may be added to the side chain, deleted from the side chain or exchanged with another functional group. Examples of severe substitutions of this type include adding an amine or hydroxyl, carboxylic acid to the aliphatic side chain of valine, leucine or isoleucine, exchanging the carboxylic acid in the side chain of aspartic acid or glutamic acid with an amine or deleting the amine group in the side chain of lysine or ornithine. In yet another alternative, the side chain of the substituting amino acid can have significantly different steric and electronic properties that the functional group of the amino acid being substituted. Examples of such modifications include tryptophan for glycine, lysine for aspartic acid and —(CH$_2$)$_4$COOH for the side chain of serine. These examples are not meant to be limiting.

A "hybrid peptide", as used herein, is an angiogenic peptide having from about 10 to about 30 amino acid residues. Each amino acid residue (naturally occurring or modified) in the amino acid sequence of a hybrid peptide is: 1) identical to the amino acid residue at the corresponding position in the AHR of a first angiogenic protein; 2) an amino acid residue structurally related thereto; 3) identical to the amino acid residue at the corresponding position in the AHR of a second angiogenic protein; or 4) an amino acid residue structurally related thereto. As noted above, replacing an amino acid residue with a structurally related amino acid residue is referred to as a "conservative substitution".

One embodiment of the present invention is a "TSP-1/endostatin hybrid peptide". Each amino acid residue of the TSP-1/endostatin hybrid is identical to or a conservative substitution of the amino acid residue at the corresponding position of TSP-1 or endostatin. In one specific example, the TSP-1/endostatin hybrid peptide is a 25-mer in which the amino acid residue at each position of the amino acid sequence is identical to the amino acid residue at the corresponding position of TSP-1 or endostatin. In another specific example, the serine residue at position seven of the 25-mer hybrid peptide described above is replaced with a threonine residue. As can be seen from FIG. 1, a serine residue is present at position seven of the amino acid sequence of the AHR of both TSP-1 and endostatin. Thus, replacement of serine with threonine represents a conservative substitution. Other specific examples include fragments of the 25-mer peptides described above having at least ten amino acid residues.

Another embodiment of the present invention is a hybrid peptide having a sequence of amino acids AA$_1$ through AA$_{28}$ or a subsequence thereof having at least ten amino acids, wherein:

AA$_1$ is lysine, ornithine, arginine, N-nitroarginine, β-cycloarginine, γ-hydroxyarginine, N-amidinocitruline 2-amino-4-guanidinobutanoic acid, glycine or alanine;

AA$_2$ is aspartic acid, asparagine, glutamic acid, glutamine, leucine, valine, isoleucine, methionine or a substituted or unsubstituted aliphatic or aryl ester of glutamic acid or aspartic acid;

AA$_3$ is phenylalanine, alanine, tyrosine, tryptophan, leucine, isoleucine, methionine, valine or glycine;

AA$_4$ is threonine, glycine, alanine, cysteine or serine;

AA$_5$ is alanine, threonine, glycine, cysteine or serine;

AA$_6$ is phenylalanine, tyrosine or tryptophan;

AA$_7$ is arginine, N-nitroarginine, β-cycloarginine, γ-hydroxyarginine, N-amidinocitruline 2-amino-4-guanidinobutanoic acid;

AA$_8$ tryptophan, alanine, phenylalanine, tyrosine or glycine;

AA$_9$ is arginine, phenylalanine, N-nitroarginine, β-cycloarginine, γ-hydroxyarginine, N-amidinocitruline 2-amino-4-guanidinobutanoic acid, lysine, ornithine, tyrosine or tryptophan;

AA$_{10}$ is leucine, isoleucine, methionine or valine;

AA$_{11}$ is serine, threonine or alanine;

AA$_{12}$ is histidine, serine, threonine, cysteine, lysine or ornithine;

AA$_{13}$ is arginine, N-nitroarginine, β-cycloarginine, γ-hydroxyarginine, N-amidinocitruline or 2-amino-4-guanidinobutanoic acid;

AA$_{14}$ is proline, leucine, valine, isoleucine or methionine;

AA$_{15}$ is lysine, glutamine, histidine, ornithine, asparagine, arginine, N-nitroarginine, β-cycloarginine, γ-hydroxyarginine, N-amidinocitruline or 2-amino-4-guanidinobutanoic acid;

AA$_{16}$ is threonine, aspartic acid, serine, glutamic acid or a substituted or unsubstituted aliphatic or aryl ester of glutamic acid or aspartic acid;

AA$_{17}$ is glycine, leucine, alanine, valine, isoleucine or methionine;

AA$_{18}$ is phenylalanine, tyrosine or tryptophan;

AA$_{19}$ is isoleucine, serine, valine, leucine, methionine, cysteine or threonine;

AA$_{20}$ is arginine, isoleucine, ornithine, lysine, N-nitroarginine, β-cycloarginine, γ-hydroxyarginine, N-amidinocitruline, 2-amino-4-guanidinobutanoic acid, leucine, valine or methionine;

AA$_{21}$ is methionine, isoleucine, leucine or valine;

AA$_{22}$ valine, arginine, leucine, isoleucine, methionine, ornithine, lysine, N-nitroarginine, βcycloarginine, γ-hydroxyarginine, N-amidinocitruline or 2-amino-4-guanidinobutanoic acid;

AA$_{23}$ methionine, arginine, leucine, isoleucine, valine, ornithine, lysine, N-nitroarginine, β-cycloarginine, γ-hydroxyarginine, N-amidinocitruline or 2-amino-4-guanidinobutanoic acid;

AA$_{24}$ is phenylalanine, alanine, tyrosine, tryptophan or glycine;

AA$_{25}$ is aspartic acid, asparagine, glutamic acid, glutamine or a substituted or unsubstituted aliphatic or aryl ester of glutamic acid or aspartic acid;

AA$_{26}$ is glycine, arginine, alanine, ornithine, lysine, N-nitroarginine, β-cycloarginine, γ-hydroxyarginine, N-amidinocitruline or 2-amino-4-guanidinobutanoic acid;

AA$_{27}$ is lysine, alanine, arginine, glycine, serine, ornithine, arginine, N-nitroarginine, β-cycloarginine, γ-hydroxyarginine, N-amidinocitruline or 2-amino-4-guanidinobutanoic acid; and AA$_{28}$ is lysine, alanine, arginine, glycine, serine, ornithine, arginine, N-nitroarginine, β-cycloarginine, γ-hydroxyarginine, N-amidinocitruline or 2-amino-4-guanidinobutanoic acid.

The hybrid peptide has angiogenic activity and is not represented by SEQ ID NO.: 1 or a subsequence thereof.

Other embodiments include hybrid peptides in which each amino acid residue of the hybrid peptide is identical to or a conservative substitution of the amino acid residue at the corresponding position of the AHR of: TSP-1 or TSP-4; TSP-1 or angiostatin; endostatin or TSP-4; endostatin or angiostatin; TSP-4 or angiostatin and TSP-1 or endostatin.

Preferably, the amino acid sequence of a hybrid peptide comprises a subsequence from a first AHR and a subsequence from a second AHR. Each subsequence has from about five to about fifteen amino acid residues. In one specific example, the first seven amino acid residues in TSP-1/endostatin hybrid correspond to a subsequence consisting of the first seven amino acid residues of the AHR of TSP-1; the last ten amino acid residues in the TSP-1/endostatin hybrid correspond to a subsequence consisting of the last ten amino acid residues of the AHR of endostatin; and amino acids eight through fourteen are identical to or a conservative substitution of the amino acid residue at the corresponding position of TSP-1 or endostatin.

More preferably, the amino acid sequence of a hybrid peptide consists of a subsequence from a first AHR and a subsequence from a second AHR. Each subsequence has from about five to about fifteen amino acid residues. The two subsequences can be equal in length, e.g., both subsequences can be 9-mers or 12-mers. Alternatively, the two subsequences can be of different lengths, e.g., a 12-mer and a 13-mer. One example, a peptide represented by SEQ ID NO.: 3, is a 22-mer in which the first eleven amino acids correspond to a subsequence of the first eleven amino acid residues of the AHR of endostatin and the second eleven amino acids correspond to a subsequence of the second eleven amino acid residues of the AHR of TSP-1. Another example, a peptide represented by SEQ ID NO.: 4, is a 22-mer in which the first eleven amino acids correspond to a subsequence of the first eleven amino acid residues of the AHR of TSP-1 and the second eleven amino acids correspond to a subsequence of the second eleven amino acid residues of the AHR of endostatin.

Another embodiment of the present invention is a peptide derivative of a hybrid peptide, for example, a peptide derivative of a peptide represented by SEQ ID NO.: 3, SEQ ID NO.: 4 or SEQ ID NO.: 9–12. Included within the definition of "peptide derivative of a hybrid peptide" are angiogenic fragments of hybrid peptides, which generally have at least about ten amino acid residues. A "peptide derivative of a hybrid peptide" also includes a peptide having a "modified sequence" in which one or more amino acids in the hybrid peptide have been substituted with a naturally occurring amino acid or amino acid analog (also referred to as a "modified amino acid"). Suitable modified sequences are those which are substantially homologous to the amino acid sequence of the hybrid peptide or to an angiogenic subsequence there. Peptide derivatives generally have between about ten and about thirty amino acid residues.

In one aspect of the present invention, a peptide derivative of a hybrid peptide, e.g., SEQ ID NOS.: 3, 4 or 9–12 has an amino acid sequence corresponding to an angiogenic subsequence of the hybrid peptide with between about ten and about fifteen amino acid residues. Zero, one, two or three amino acid residues in the peptide derivative can differ from the amino acid residue(s) in the corresponding position of the subsequence of the hybrid peptide.

In another aspect of the present invention, a peptide derivative has an amino acid sequence corresponding to the amino acid sequence of the hybrid peptide or to an angiogenic subsequence thereof with between about sixteen and about twenty-eight amino acid residues. Zero, one, two, three or four amino acid residues in the peptide derivative can differ from the amino acid residue(s) in the corresponding position of the sequence or subsequence of the hybrid peptide.

Optionally, the C-terminus or the N-terminus of the peptides of the present invention, or both, can be substituted with a carboxylic acid protecting group or an amine protecting group, respectively. Suitable protecting groups are described in Green and Wuts, "*Protecting Groups in Organic Synthesis*", John Wiley and Sons, Chapters 5 and 7, 1991, the teachings of which are incorporated herein by reference. As with protecting groups for functional groups found in the amino acid residue side chains, preferred protecting groups are those which facilitate transport of the peptide into a cell, for example, by reducing the hydrophilicity and increasing the lipophilicity of the peptide. Examples of N-terminal protecting groups include acyl groups (—CO—$R_1$) and alkoxy carbonyl or aryloxy carbonyl groups (—CO—O—$R_1$), wherein $R_1$ is an aliphatic, substituted aliphatic, benzyl, substituted benzyl, aromatic or a substituted aromatic group. Specific examples of acyl groups include acetyl, (ethyl)-CO—, n-propyl-CO—, iso-propyl-CO—, n-butyl-CO—, sec-butyl-CO—, t-butyl-CO—, phenyl-CO—, substituted phenyl-CO—, benzyl-CO—, (substituted benzyl)-CO— and myristoyl. Examples of alkoxy carbonyl and aryloxy carbonyl groups include $CH_3$—O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and benzyl-O—CO—, (substituted benzyl)-O—CO—. The carboxyl group at the C-terminus can be protected, for example, as an amide (i.e., the hydroxyl group at the C-terminus is replaced with —$NH_2$, —$NHR_2$ and —$NR_2R_3$) or ester (i.e. the hydroxyl group at the C-terminus is replace with —$OR_2$). $R_2$ and $R_3$ are independently an aliphatic, substituted aliphatic, benzyl, substituted benzyl, aryl or a substituted aryl group. In addition, taken together with the nitrogen atom, $R_2$ and $R_3$ can form a C4 to C8 heterocyclic ring with from about 0–2 additional heteroatoms such as nitrogen, oxygen or sulfur. Examples of suitable heterocyclic rings include piperidinyl, pyrrolidinyl, morpholino, thiomorpholino or piperazinyl. Examples of C-terminal protecting groups include —$NH_2$, —$NHCH_3$, —$N(CH_3)_2$, —NH(ethyl), —$N(ethyl)_2$, —N(methyl)(ethyl), —NH(benzyl), —N(C1–C4 alkyl)(benzyl), —NH(phenyl), —N(C1–C4 alkyl)(phenyl), —$OCH_3$, —O-(ethyl), —O-(n-propyl), —O-(n-butyl), —O-(iso-propyl), —O-(sec-butyl), —O-(t-butyl), —O-benzyl and —O-phenyl.

As used herein, aliphatic groups include straight chained, branched or cyclic C1–C6 hydrocarbons which are completely saturated, which contain one or two heteroatoms such as nitrogen, oxygen or sulfur and/or which contain one or more units of unsaturation. Aromatic groups include carbocyclic aromatic groups such as phenyl and naphthyl and heterocyclic aromatic groups such as imidazolyl, indolyl, thienyl, furanyl, pyridyl, pyranyl, pyranyl, oxazolyl, benzothienyl, benzofuranyl, quinolinyl, isoquinolinyl and acridintyl.

Suitable substituents on an aliphatic, aromatic or benzyl group include, for example, —OH, halogen (—Br, —Cl, —I and —F) —O(aliphatic, substituted aliphatic, benzyl, substituted benzyl, aryl or substituted aryl group), —CN, —$NO_2$, —COOH, —$NH_2$, —NH(aliphatic group, substituted aliphatic, benzyl, substituted benzyl, aryl or substituted aryl group), —N(aliphatic group, substituted aliphatic, benzyl, substituted benzyl, aryl or substituted aryl group)$_2$, —COO(aliphatic group, substituted aliphatic, benzyl, substituted benzyl, aryl or substituted aryl group), —$CONH_2$, —CONH(aliphatic, substituted aliphatic group, benzyl, substituted benzyl, aryl or substituted aryl group)), —SH, —S(aliphatic, substituted aliphatic, benzyl, substituted benzyl, aromatic or substituted aromatic group) and —NH—C(=NH)—$NH_2$. A substituted benzylic or aromatic group can also have an aliphatic or substituted aliphatic group as a substituent. A substituted aliphatic group can also have a benzyl, substituted benzyl, aryl or substituted aryl group as a substituent. A substituted aliphatic, substituted aromatic or substituted benzyl group can have more than one substituent.

A "multivalent ligand" is a molecule having an array peptides, preferably from two to about twenty peptides. Each peptide is connected to a multilinker backbone, either by a covalent bond or through a linker group. Each peptide derivative and each linker or covalent bond is independently chosen. A multivalent ligand is represented by Structural Formula (I).

A "polypeptide multivalent ligand" is a tandem repeat polypeptide chain in which two or more peptides P are each separated by a peptide spacer. A polypeptide multivalent ligand is represented by Structural Formula (II).

At least two of the peptides P in a multivalent ligand or the polypeptide multivalent ligand of the present invention are hybrid peptides, peptide derivatives of hybrid peptides, peptide derivatives of AHRs, or combinations thereof. A multivalent ligand or a polypeptide multivalent ligand can also have one or more other peptides P which do not significantly lower its angiogenic activity. Preferably, however, all of the peptides P in a multivalent ligand or a polypeptide multivalent ligand are hybrid peptides, peptide derivatives of hybrid peptides, and/or peptide derivatives of an AHR. Optionally, the C-terminus or the N-terminus of a polypeptide multivalent ligand can include amino acid sequences which might assist in its separation, such as hemagglutinin-antigen or His-Tag. A multivalent ligand or a polypeptide multivalent ligand can have peptides P which are derivatives of different AHRs and/or peptides P which are derivatives of the same AHR but which have different amino acid sequences. A multivalent ligand or a polypeptide multivalent ligand can have peptides P which are hybrids of a different pair of AHRs and/or peptides which are hybrids of the same two AHRs but which have different amino acid sequences. Similarly, a multivalent ligand or a polypeptide multivalent ligand can have peptides P which are derivatives of different hybrid peptides and/or peptides p which are derivatives of the same hybrid peptide but which have different amino acid sequences. More preferably, however, the peptides of a multivalent ligand or a polypeptide multivalent ligand are all the same.

Figure 12:
FIG. 12 is a diagram showing a polypeptide multivalent ligand represented by SEQ ID NO.: 15.
Figure 12:
Figure 12:

Examples of multivalent ligands are described in the Table. An example of a polypeptide multivalent ligand is shown in FIG. 12 and is represented by SEQ ID NO.: 15. Other examples include wherein Tip-19.40 in SEQ ID NO.: 15 is replaced by Tip-12.40, Tip-13.40, Tip-14.40, Tip-15.40, Tip-16.40, Tip-17.40 or Tip-18.40, and/or wherein the polypeptide multivalent ligand has from one to twenty peptide spacers.

A multilinker backbone is a linear or branched molecule having a multiplicity of appropriately spaced reactive groups, each of which can react with a functional group in a peptide or linker. Suitable multilinker backbones are biocompatible and, after attachment of the peptide derivatives, are suitable for parenteral or oral administration. Generally, the multilinker backbones have molecular weights less than about 20,000 atomic mass units (amu) and typically comprise between two to about a hundred attachment sites. Not all attachment sites need be occupied.

Reactive functional groups in a multilinker backbone serve as attachment sites for the peptides or linkers. Attachment sites are "appropriately spaced" when 1) steric hindrance does not substantially interfere with forming covalent bonds between some of the reactive functional groups and the peptide.

Suitable reactive groups in a multilinker backbone include amines, carboxylic acids, alcohols, aldehydes and thiols. An amine group in a multilinker backbone can form a covalent bonds with the C-terminal of a peptide derivative or a carboxylic acid functional group in a linker group. A carboxylic acid group or an aldehyde in a multilinker backbone form a covalent bond with the N-terminus of a peptide derivative or an amine group in a linker group. An alcohol group in a multilinker backbone can form a covalent bond with the C-terminus of a peptide derivative or a carboxylic acid group in a linker group. A thiol group in a multilinker backbone can form a disulfide bond with a cysteine in a peptide derivative or a thiol group in a linker group. Bonds can also be formed between reactive functional groups in the multilinker backbone and appropriate functional groups in the amino acid side chains of the attached peptides, as described above. The functionality which connects each peptide to the multilinker backbone can be different, but is preferably the same for all peptides.

Examples of suitable multilinker backbones include polymers with pendant reactive groups such as [—($CH_2$)$_n$—CHR($NH_2$)—]$_m$, [—CHR$NH_2$—]$_m$, [—($CH_2$)$_n$—CHR(COOH)—]$_m$ (R is, for example, an aliphatic or aryl group), polyethylene glycols and polypeptides polyvinyl pyrollidones and derivatives thereof, and aromatic polymers are represented by, for example, by the following Structural Formula:

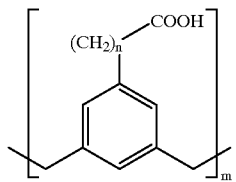

Also included are polyurethane multilinker backbones, examples of which are disclosed in Lin et al., *J. Biomed. Material. Res.* 28:329 (1994), the entire teachings of which are incorporated herein by reference. Polypeptides are preferred multilinker backbones.

Examples of suitable polypeptide multivalent backbones are disclosed in Tam, *Journal of Immunological Methods* 196:17 (1996), the entire teachings of which are incorporated herein by reference. Suitable polypeptide multilinker backbones generally have between about three and about forty amino acid residues. As with other multilinker backbones, they typically have between about two and about twenty attachment sites, which are often functional groups located in the amino acid residue side chains. However, alpha amino groups and alpha carboxylic acids can also serve as attachment sites.

Preferred polypeptide multilinker backbones include polylysines, polyornithines, polycysteines, polyglutamic acid and polyaspartic acid. Optionally, amino acid residues with inert side chains, e.g., glycine, alanine and valine, can be included in the amino acid sequence. The polypeptides can be pennant or cascading. A "pennant polypeptide" is linear. As with polypeptides typically found in nature, the amide bonds of a pennant polypeptide are formed between the alpha amine of one amino acid residue and the alpha carboxylic acid of the next amino acid residue. When n is less than five, there are typically 0–6 amino acids between attachment sites; when n is greater than five, there are typically 1–6 amino acids between attachment sites. A "cascading polypeptide" is branched with at least some of the amide bonds formed between the side chain functional group of one amino acid residue and the alpha amino group or alpha carboxylic acid group of the next amino acid residue. For example, at least some of the amide bonds of a cascading polylysine are formed between the epsilon amine group of a lysine residue and the carboxylic acid residue of the next lysine residue. Examples of cascading and pennant polylysines are shown in FIGS. 4A through 4D.

Suitable linkers are inert groups which can connect a peptide derivative to a multilinker backbone. In one example, the linker is an oligopeptide of from about one to about 10 amino acids consisting of amino acids with inert side chains. Suitable oligopeptide include polyglycine, polyserine, polyproline, polyalanine and oligopeptides consisting of alanyl and/or serinyl and/or prolinyl and/or glycyl amino acid residues. In another example, the linker is $X_1$—($CH_2$)$_m$—$X_2$ or $X_1$-polyethylene-glycol-$X_2$. $X_1$ and $X_2$ are the residues of a functional group which is connected by a covalent bond to a suitable functional group residue in the multilinker backbone or peptide derivative, respectively. Examples of $X_1$ and $X_2$ include: 1) the residue of an alcohol group which forms an ester with the residue of a carboxylic acid group in the multilinker backbone or peptide derivative; 2) the residue of an amine group which forms an amide with the residue of a carboxylic acid group in the multilinker backbone or peptide derivative; 4) the residue of a carboxylic acid or aldehyde group which forms an amide with the residue of an amine in the multilinker backbone or peptide derivative; or 5) the residue of a thiol group which forms a dissulfide with the residue of a thiol group in the multilinker backbone or peptide derivative. m is an integer from two to about 20.

The peptides in a multivalent ligand can be connected to the multilinker backbone by covalent bonds, linker groups or a combination thereof. The linking groups can be the same or different. Preferably, every peptide in a multivalent ligand is connected to the multilinker backbone by a covalent bond. Alternatively, every peptide in a multivalent ligand is connected to the multilinker backbone by the same linking group, e.g., a glycine residue or a glycyl-glycyl dipeptide.

Examples of multivalent ligands are referred to herein as Tip-12.40, Tip-13.40, Tip-14.40, Tip-15.40, Tip-16.40, Tip-17.40, Tip-18.40 and Tip-19.40. These multivalent ligands are four-branch penannt polylysine trimers, indicating that four peptides are attached to a linear trimeric polypeptide backbone consisting of three lysine residues. The attachment is by means of a peptide bond between the C-terminus of each peptide or linking oligopeptide and the amino group in one of the three lysine side chains or the N-terminus of the polylysine. All peptides and all linkers in a given multivalent ligand are the same. Further structural information is provided below in the Table:

TABLE

| Multivalent Ligand | Sequence of Each Peptide | Linking Group |
|---|---|---|
| Tip-12.40 | Represented by SEQ ID NO.: 7 | Covalent Bond |
| Tip-13.40 | Represented by SEQ ID NO.: 8 | Covalent Bond |
| Tip-14.40 | Represented by SEQ ID NO.: 3 | Covalent Bond |
| Tip-15.50 | Represented by SEQ ID NO.: 4 | Covalent Bond |
| Tip-16.40 | Represented by SEQ ID NO.: 10 | —Gly—Gly— |
| Tip-17.40 | Represented by SEQ ID NO.: 9 | —Gly—Gly— |
| Tip-18.40 | Represented by SEQ ID NO.: 11 | —Gly—Gly— |
| Tip-19.40 | Represented by SEQ ID NO.: 12 | —Gly—Gly— |

A polypeptide spacer S, shown in Structural Formula (II), is a peptide having from about five to about forty amino acid residues. The spacers in a polypeptide multivalent ligand are independently chosen, but are preferably all the same. The spacers should allow for flexibility of movement in space for the flanking peptides P, and are therefore typically rich in small amino acids, for example, glycine, serine, proline or alanine. Preferably, peptide spacers contain at least 60%, more preferably at least 80% glycine or alanine. In addition, peptide spacers generally have little or no biological and antigenic activity. Preferred spacers are $(Gly-Pro-Gly-Gly)_x$ and $(Gly_4-Ser)_y$, wherein x is an integer from about three to about nine and y is an integer from about one to about eight. Specific examples of suitable spacers include $(Gly_4-Ser)_3$ (SEQ ID NO.: 13) or $(Gly_4-Ser)_4$ (SEQ ID NO.: 14). Spacers can also include from one to about four amino acids which create a restriction site, but which are nonangiogenic and which are not biologically active.

The multivalent ligands and polypeptide multivalent ligands of the present invention are angiogenic agents and can therefore be used to modulate angiogenesis in a subject or individual. A "subject" is preferably a human, but can also be animals in need of treatment, e.g., veterinary animals (e.g., dogs, cats, and the like), farm animals (e.g., cows, pigs, horses and the like) and laboratory animals (e.g., rats, mice, guinea pigs and the like).

Angiogenic agents, including the multivalent ligands and polypeptide multivalent ligands disclosed herein, can be used to treat a wide variety of disease conditions, including cancer, cardiovascular diseases (e.g., arteriosclerosis, ischaemic limbs and ischaemic myocardium) obesity, osteoarthritis, duodenal ulcers, and abnormal ocular neovascularization associated, for example, with diabetes mellitus.

A "therapeutically effective amount" is the quantity of compound which results in an improved clinical outcome as a result of the treatment compared with a typical clinical outcome in the absence of the treatment. Alternatively, an "improved clinical outcome" includes a longer life expectancy for subjects with the disease as a result of the treatment or results in the subject with the disease experiencing fewer symptoms or complications of the disease as a result of the treatment. With respect to cancer, an "improved clinical outcome" includes a longer life expectancy. Alternatively, it can include slowing or arresting the rate of growth of a tumor, causing a shrinkage in the size of the tumor, a decreased rate of metastasis and/or improved quality of life (e.g., a decrease in physical discomfort or an increase in mobility).

With respect to abnormal ocular neovascularization associated, for example, with diabetes, "improved clinical outcome" refers to slowing, retarding or reversing the loss of sight associated with the disease. Alternatively, it refers to a reduction in retinopathy.

With respect to obesity, an improved clinical outcome refers to increased weight reduction per calory intake. Alternatively, it refers to a decrease in the complications which are a consequence of obesity, for example heart disease such as arteriosclerosis and high blood pressure.

With respect to osteoarthritis, an improved clinical outcome refers to slowing, arresting or reversing the degradation and loss of function typical observed in a joint afflicted with osteoarthritis, e.g. by reducing the rate of cartilage degradation in the joint. Alternatively, it refers to lessening the pain and/or inflammation associated with osteoarthritis.

With respect to wound healing, an improved clinical outcome can refer to a more rapid rate of wound closure, less wound contraction and/or less scaring.

With respect to neovascularization to bypass occluded blood vessels, a "therapeutically effective amount" is a quantity which results in the formation of new blood vessels which can transport at least some of the blood which normally would pass through the blocked vessel.

The amount of the multivalent ligands or polypeptide multivalent ligands administered to the subject will depend on the type and severity of the disease and on the characteristics of the subject, such as general health, age, sex, body weight and tolerance to drugs. The skilled artisan will be able to determine appropriate dosages depending on these and other factors. Typically, a therapeutically effective amount of the multivalent ligand can range from about 1 mg per kilogram body weight per day to about 1000 mg per kilogram body weight per day for an adult. Preferably, the dosage ranges from about 1 mg per kilogram body weight per day to about 100 mg per kilogram body weight per day.

The multivalent ligands and polypeptide multivalent of the present invention can, for example, be administered orally or parenterally. Parenteral administration can include, for example, systemic administration, such as by intramuscular, intravenous, subcutaneous, or intraperitoneal injection.

The multivalent ligands and polypeptide multivalent ligands can be administered to the subject in conjunction with an acceptable pharmaceutical carrier as part of a pharmaceutical composition for treating the diseases discussed above. Suitable pharmaceutical carriers may contain inert ingredients which do not interact with the peptide or peptide derivative. Standard pharmaceutical formulation techniques may be employed such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., *Controlled Release of Biological Active Agents*, John Wiley and Sons, 1986).

When used to promote wound healing, a multivalent ligand or polypeptide multivalent ligand be applied directly to the wound as part of a pharmaceutical formulation which includes a pharmaceutical carrier. Examples of pharmaceutically acceptable carriers include, for example, commercially available inert gels, or liquids supplemented with albumin, methyl cellulose or a collagen matrix. Typical of such formulations are ointments, creams and gels. Ointments are typically prepared using an oleaginous base, e.g., containing fixed oils or hydrocarbons, such as white petrolatum or mineral oil, or an absorbent base, e.g., consisting of an absorbent anhydrous substance or substances, for example anhydrous lanolin. Following formation of the base, the active ingredients are added in the desired concentration. Creams generally comprise an oil phase (internal phase) containing typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, beegum, and the like. Upon formation of the emulsion, the active ingredients are added in the desired concentration. Gels are comprised of a base selected from an oleaginous base, water, or an emulsion-suspension base, as previously described. To the base is added a gelling agent which forms a matrix in the base, increasing its viscosity to a semisolid consistency. Examples of gelling agents are hydroxypropyl cellulose, acrylic acid polymers, and the like. The active ingredients are added to the formulation at the desired concentration at a point preceding addition of the gelling agent.

The multivalent ligands or polypeptide multivalent ligands of the present invention can be co-administered with other pharmaceutically active agents. In one example, the multivalent ligands or polypeptide multivalent ligands are co-administered with other anti-cancer agents when used to treat a subject with cancer.

The peptide derivatives, the multivalent ligands and or polypeptide multivalent ligands of the present invention have many utilities other than for therapy. Some of these uses are discussed in the following paragraphs.

The disclosed multivalent ligands can be used to raise antibodies, both polyclonal and monoclonal, against the peptide derivatives attached thereto. Methods of raising antibodies against peptide antigens attached to a multilinker backbone are described in Tam, *Proc. Natl. Acad. Sci. USA* 85:5409 (1988), Tam and Lu, *Proc. Natl. Acad. Sci. USA* 86:9084 (1989 and Tam, *Journal of Immunological Methods* 196:17 (1996), the entire teachings of which are incorporated herein by reference.

Suitable antibodies can also be raised against the peptide derivatives and hybrid peptides of the present invention by conjugating to a suitable carrier, such as keyhole limpet hemocyanin or serum albumin; polyclonal and monoclonal antibody production can be performed using any suitable technique. A variety of methods for producing monoclonal antibodies have been described (see e.g., Kohler et al., *Nature*, 256: 495–497 (1975) and *Eur. J. Immunol.* 6: 511–519 (1976); Milstein et al., *Nature* 266: 550–552 (1977); Koprowski et al., U.S. Pat. No. 4,172,124; Harlow, E. and D. Lane, 1988, *Antibodies: A Laboratory Manual*, (Cold Spring Harbor Laboratory: Cold Spring Harbor, N.Y.); *Current Protocols In Molecular Biology*, Vol. 2 (Supplement 27, Summer 1994), Ausubel, F. M. et al., Eds., (John Wiley & Sons: New York, N.Y.), Chapter 11, (1991)). Generally, a hybridoma can be produced by fusing a suitable immortal cell line (e.g., a myeloma cell line such as SP2/0) with antibody producing cells. The antibody producing cell, preferably those of the spleen or lymph nodes, can be obtained from animals immunized with the antigen of interest. The fused cells (hybridomas) can be isolated using selective culture conditions, and cloned by limiting dilution. Cells which produce antibodies with the desired specificity can be selected by a suitable assay (e.g., ELISA).

Antibodies, including monoclonal antibodies, against the AHR of angiogenic proteins have a variety of uses. For example, those against or reactive with an angiogenic protein, and preferably which bind specifically to the AHR of said protein, can be used to determine if the angiogenic protein is present in a liquid sample obtained from a subject. The sample is treated with anti-AHR antibody specific for the angiogenic protein. The sample is then analzyed, for example, by Western blotting or immunoprecipitation for complexes between the angiogenic protein and antibody. The sample can be, for example, a cleared lysate of a cell, which is generated for example, by treating cells with a detergent such as sodium deoxycholate (0.5%–1%) or sodium dodecyl sulfate (1%), centrifugating and separating the supernatant from the pellet.

AHRs play a key role in the biological activity of angiogenic proteins, as is evidenced by the fact that multivalent ligands comprising the peptide derivatives or hybrid peptides of the present invention have such a dramatic effect on biological processes such as tumor growth. The polypeptide multivalent ligands, peptide derivatives and hybrid peptides of the present invention can also be used to identify molecules which interact with the AHR of specific angiogenic proteins and whose activities are modulated by them. For example, an affinity column can be prepared to which a specific polypeptide multivalent ligand, peptide derivative or hybrid peptide is covalently attached, directly or via a linker. This column, in turn, can be utilized for the isolation and identification of specific molecules which bind the AHRs of angiogenic proteins and which will also likely bind the angiogenic protein from which the peptide derivative was derived. The molecule can then be eluted from the column, characterized and tested for its ability to interact with angiogenic proteins.

Peptide sequences in the compounds of the present invention may be synthesized by solid phase peptide synthesis (e.g., BOC or FMOC) method, by solution phase synthesis, or by other suitable techniques including combinations of the foregoing methods. The BOC and FMOC methods, which are established and widely used, are described in Merrifield, *J. Am. Chem. Soc.* 88:2149 (1963); Meienhofer, *Hormonal Proteins and Peptides*, C. H. Li, Ed., Academic Press, 1983, pp. 48–267; and Barany and Merrifield, in *The Peptides*, E. Gross and J. Meienhofer, Eds., Academic Press, New York, 1980, pp. 3–285. Methods of solid phase peptide synthesis are described in Merrifield, R. B., *Science*, 232: 341 (1986); Carpino, L. A. and Han, G. Y., *J. Org. Chem.*, 37: 3404 (1972); and Gauspohl, H. et al., *Synthesis*, 5: 315 (1992)). The teachings of these references are incorporated herein by reference.

Multivalent ligands can be prepared by methods known in the art, including methods disclosed in Tam, *J. of Immunological Methods* 196:17 (1996), Kim et al., *Cancer Research* 54:5005 (1994), Nomizu et al., *Cancer Research* 53:3459 (1993) and Tam, *Proc. Natl. Acad. Sci., USA* 85:5409 (1989), the teachings of which are incorporated herein by reference.

A convenient method of preparing multivalent ligands in a single operation is by stepwise solid phase synthesis, starting with the C-terminus core matrix using a diprotected Boc-Lys(Boc) in Boc chemistry or Fmoc-Lys(Fmoc) in Fmoc chemistry to reach the desired branching. The selected peptide derivative, hybrid peptide or hybrid peptide derivative is then sequentially elongated to the lysinyl core matrix on the resin to form the desired mutlivalent ligand. This stepwise method produces multivalent ligands with a C→N orientation. Chimeric multivalent ligands having two or more different appended peptides can be also produced in this way by tandemly synthesizing both sequences in a continuous array. Alternatively, different peptides can be synthesized on the different arms of the core matrix, using a core matrix bearing two different amine-protecting groups. Methods to distinguish the α and ε-mines of lysines so that different peptides and functional moieties could be introduced have been developed. A common theme in these methods is the manipulation of the orthogonality or differential liability of deprotecting methods. Suitable combinations include: (i) Boc-Fmoc (Tam and Lu, *Proc. Natl. Acad. Sci., USA* 86:9084 (1989); (ii) Fmoc-Dde (Bycroft et al., *J. Chem. Soc. Chem. Commun.* 1993:773 (1993); and (iii) Npys-Fmoc (Ahlborg, *J. Immunol. Methods* 179:269 (1995). The entire teachings of these references are incorporated herein by reference.

A polynucleotide encoding a polypeptide multivalent ligand represented by Structural Formula (II) can be prepared by methods disclosed in Lake et al., *Biotechniques* 19:700 (1995), the entire teachings of which are incorporated herein by reference. Alternatively, this gene, encoding the polypeptide multivalent ligand represented by Structural Formula (II), can be prepared by synthesizing several separate primers with overlapping regions and then anneal them together, using commonly available automated DNA synthesizers. Following ligation of the annealed polynucleotide, the DNA which code for the desired periodicity of the multivalent ligand can be then selected by its size and its DNA sequence. Once prepared, a polynucleotide encoding a polypeptide multivalent ligand can be expressed using standard recombinant DNA technology. Specifically, the polynucleotide is introduced into a suitable amplifying organism (e.g., *E. coli* of yeast) using an appropriate plasmid vector; the resulting amplifying organism, which contains the polynucleotide, is maintained under conditions suitable for the polynucleotide to be expressed and reproduced by the amplifying organism. Suitable plasmid vectors typically contain an origin of replication (e.g. an autonomously replicating sequence when the plasmid is transformed into yeast), a yeast centromere and a growth origin suitable for growth and replication in the tester cells being transformed. The plasmid vector also contains a gene allowing for selection in the amplifying organism being transformed, e.g. a gene conferring resistance to an antibiotic provided in the growth medium or allowing the expression cells to metabolize an essential nutrient supplied in the growth medium (for example trp). Typically, the plasmid also comprises genes suitable for selection and growth in an amplifying organism. Optionally, the plasmid can contain one or more polycloning sites and/or a gene (e.g. lacz gene) which indicates incorporation of the transforming DNA into the plasmid. Plasmids are introduced into the cells of an amplifying organism by methods known in the art, for example, by the calcium phosphate method, electroporation or lithium chloride. Suitable plasmids also have promoter sites which allow the gene being assessed to be efficiently expressed in the amplifying organism (e.g. SV40, gal 10 or other viral promoters). Specific experimental protocols are disclosed in "Molecular Cloning", by Sambrook J., Fritsch E. F. and Maniatis, T. Cold Spring Harbor Laboratory Press, second edition (1989), the entire teachings of which are incorporated herein by reference.

Other procedures for preparing polypeptide multivalent ligands are disclosed in Rötzschlee et al., *Proc. Natl. Acad. Sci. USA* 94:1462 (1997), the entire teachings of which are incorporated herein by reference.

The invention is illustrated by the following examples which are not intended to be limiting in any way.

EXEMPLIFICATION

EXAMPLE 1

Preparation of Multivalent Ligands

The synthesis of a tetra branched matrix core with an AHR-peptide attached was accomplished manually by a stepwise solid-phase procedure (Merrifield, R. B., *J. Am. Chem. Soc.*, 85:2149–2154 (1963) on t-butoxycarbonyl (Boc) βAla-OCH$_2$-Pam resin (Mitchell, A. R., et al., *J. Org. Chem.*, 43:2845–2852 (1978) in which 0.05 mmol of βAla is present in 0.5 g of resin. The synthesis of the first and every subsequent level of the carrier core was achieved using a 4 M excess of preformed symmetrical anhydride of $N^\alpha,N^\epsilon$-Boc-Lys(Boc) (0.2, 0.4, 0.8 and 1.6 mmol consecutively) in dimethylformamide (HCONMe$_2$, 12 ml/g resin) followed by a second coupling via dicyclohexylcarbodiimide alone in CH$_2$Cl$_2$ to give, after deprotection, the tetra-branched core matrix containing four functional amino groups. The protecting groups for the synthesis of the peptide antigens were Boc groups for the α-amino termini and benzyl alcohol derivatives for most side-chain amino acids. For all residues except arginine, asparagine, glutamine, and glycine, the first coupling for 1 hour, monitored by quantitative ninhydin test (Sarin, V. K., et al., *Anal. Biochem.*, 117:147–157 (1981) was done with the preformed symmetrical anhydride in CH$_2$Cl$_2$, a second coupling in HCONMe$_2$, and a third (if needed) in N-methylpyrrolidone at 50° C. (Tam, J. P., in *Proceedings of the Ninth American Peptide Symposium*, eds. Deber, C. M., Kopple, K. D. and Hruby, V. J. (Pierce Chem., Rockford, Ill.) pp. 305–308 (1985)). The coupling of Boc-Asn and Boc-Gln was mediated by the preformed 1-hydroxybenzotriazole ester in HCONMe$_2$. Boc-Gly and Boc-Arg were coupled with water-soluble dicyclohexylcarbodiimide alone to avoid, respectively, the risk of formation of dipeptide and lactam. To eliminate the polycationic amino groups, which give highly charged macromolecules, the peptide chains were capped on their α-amino group by acetylation if 3 mM acetic anhydride in HCONMe$_2$ containing 0.3 mmol of N,N-dimethylaminopyridine at the completion of the multivalent ligand. The deprotection process was initiated by removing the dinitrophenyl protecting group of His(Dnp) with 1 M thiophenol in HCONMe$_2$ for 8 hours (3 times and at 50° C. if necessary to complete the rection). The branched peptide oligolysine was removed from the crosslinked polystyrene resin support with the low-high-HF method or the low-high trifluoromethanesulfonic-sulfonic acid method of cleavage to yield the crude multivalent ligand (85%–93% clevage yield) (Tam, J. P., et al., *J. Am. Chem. Soc.*, 108:5242–5251 (1986). The crude peptide and resin were then washed with cold ether/mercaptoethanol (99:1, vol/vol., 30 ml) to remove ρ-thiocresol and ρ-cresol, and the peptide was extracted with 100 ml of 8M urea/0.2 M dithiothreitol/0.1 M Tris-HCl buffer, pH 8.0. To remove all the remaining aromatic by-products generated in the cleavage step, the peptide was dialyzed in Spectrum Por 6 tubing, 1000 M, cutoff by equilibration for 24 hours with a deacrated and N$_2$-purged solution containing 8 M urea, 0.1 M NH$_4$HCO$_3$/(NH$_4$)$_2$CO$_3$, pH 8.0, with 0.1 M mercaptoethanol at 0° C. for 24 hours. The dialysis was then continued in 8 M and then in 2 M urea— all in 0.1 M NH$_4$HCO$_3$/(NH$_4$)$_2$CO$_3$ buffer, pH 8.0 for 12 hours and then sequentially in H$_2$O and 1 M HOAc to remove all urea. The multivalent ligand was lyophilized and purified batchwise by high-performance gel-permeation or ion-exchange chromatography. All purified materials were analyzed and found to contain the predicted amino acid sequences.

EXAMPLE 2

Multivalent Ligands Modulate Tumor Growth in Mice

B16 melanoma cells were injected into 7–8 week old female C57BL mice or CBF1 mice, S.C., $2\times10^5$ cells per mouse, in 0.1 ml volume. One week after the tumor innoculation, the treatment was started by S.C. injection at sites remote from the tumor of the indicated multivalent ligand at a dose 20–30 mg/kg body weight/day for a period of two weeks. Tumors were measured with a dial-caliper and volumes were determined using the formula: $(width)^2 \times length \times 0.52$. Each group (experimental or control) contained 5–6 mice. FIGS. 6–9 depict changes in mean tumor-volume over time.

As can be seen from FIGS. 6–9, Tip-12.40, Tip-13.40, Tip-16.40, Tip-18.40 and Tip-19.40 suppressed tumor growth, whereas Tip-17.40 promoted tumor growth. Tip-14.40 and Tip-15.40 were also tested and showed weak, but statistically significant inhibition of B16 melanoma tumor growth in mice.

EXAMPLE 3

Multivalent Ligands Inhibit the Proliferation of Bovine Aortic Endothelial Cells In Vitro The experiments were performed using 96 well, flat bottom, tissue culture microtiter plates. Culture medium was prepared from DMEM, penicillin (100 U/ml), streptomycin (100 µg/ml), glutamine (2 mM), 10% endotoxin free bovine calf serum (Hyclone) and 1 ng/ml of basic fibroblast growth factor (any commericial source).

Bovine aortic endothelial cells (referred to herein as "A19 cells") were obtained by procedures disclosed in Gospodorowicz et al., *Proc. Natl. Acad. Sci. USA* 73:4120 (1976), the entire teachings of which are incorporated herein by reference. An A19 cell suspension at $25\times10^3$ cells/ml was prepared in the above described culture medium and distributed 0.160 ml/well (about 4000 endothelial cells/well).

Multivalent ligand peptides Tip-18.40 and Tip-19.40 stock solutions was prepared by diluting a 10 mM solution of the HJ peptide in 100% DMSO with phosphate buffered saline (PBS)containing 0.1% BSA. The concentration of HJ peptide in each stock solution was adjusted to nine times the desired concentration of the HJ peptide in the assay mixture.

0.020 ml of each HJ peptide stock solution was added to the corresponding wells about 2 hours after BCE plating, with six replicates for each concentration. In addition, BSA solution with no added HJ peptide was used as a control. The wells were incubated for 72–80 hours at 37° C. in a 10% $CO_2$ humidified incubator.

The plates were labeled and the medium discarded. Each plate was then washed one time with PBS (0.200 ml/well). The wells were fixed with 4% formaldehyde PBS (PBS buffered 10% formalin from Fisher Scientific; Catalog No. HC200-1) (0.12 ml/well) for at least 30 minutes.

The wells were washed one time with borate buffer (0.1 M, pH 8.5). Freshly filtered 1% methylene blue solution (0.060 ml/well) was then added to the wells and incubated for 10 minutes at room temperature. The wells were then washed five times with tap water, after which the wells were dried completely. 0.200 ml/well of 0.1 N HCl (0.1 N) was added to extract the color. After extracting overnight, the O.D. was read at 630 nm to determine the relative number of cells per well. The procedure for counting cells is described in greater detail in Oliver et al., *J. of Cell Sci.*, 92:513 (1989), the teachings of which are incorporated herein by reference.

Figure 10:
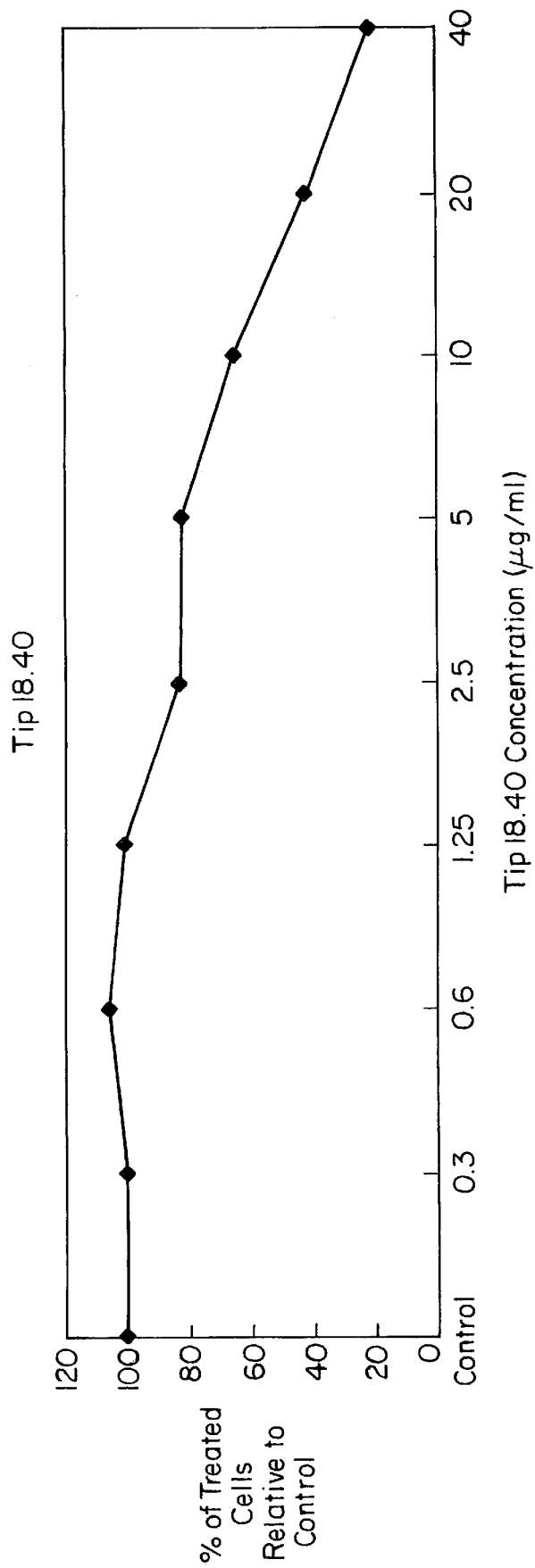
FIG. 10 is a graph showing the effect of increasing concentrations of Tip-18.40, measured in $\mu$g/ml, on bovine aortic endothelial cells proliferation in vitro, measured as the percentage treated cells growing in culture relative to untreated cells.
Figure 11:
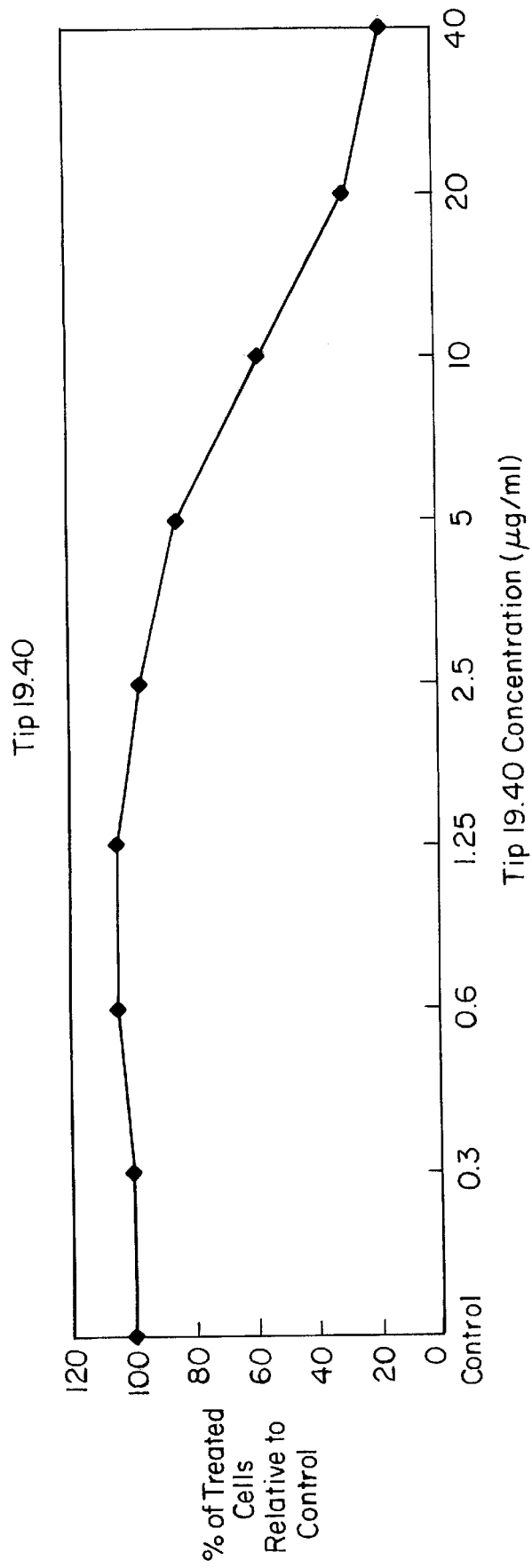
FIG. 11 is a graph showing the effect of increasing concentrations of Tip-19.40, measured in $\mu$g/ml, on bovine aortic endothelial cells proliferation in vitro, measured as the percentage treated cells growing in culture relative to untreated cells.

The results are shown in FIGS. 10 and show that Tip-18.40 and Tip-19.40 both inhibit the proliferation of bovine aortic endothelial cells in vitro.

Equivalents

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

---

What is claimed is:

1. A peptide comprising a sequence of amino acids $AA_1$ through $AA_{28}$ or a subsequence thereof having at least ten amino acids, wherein:

$AA_1$ is lysine, ornithine, arginine, N-nitroarginine, β-cycloarginine, γ-hydroxyarginine, N-amidinocitruline, 2-amino-4-guanidinobutanoic acid, glycine or alanine;

$AA_2$ is aspartic acid, asparagine, glutamic acid, glutamine, leucine, valine, isoleucine, methionine or a substituted or unsubstituted aliphatic or aryl ester of glutamic acid or aspartic acid;

$AA_3$ is phenylalanine, alanine, tyrosine, tryptophan, leucine, isoleucine, methionine, valine or glycine;

$AA_4$ is threonine, glycine, alanine, cysteine or serine;

$AA_5$ is alanine, threonine, glycine, cysteine or serine;

$AA_6$ is phenylalanine, tyrosine or tryptophan;

$AA_7$ is arginine, N-nitroarginine, β-cycloarginine, γ-hydroxyarginine, N-amidinocitruline or 2-amino-4-guanidinobutanoic acid;

$AA_8$ tryptophan, alanine, phenylalanine, tyrosine or glycine;

$AA_9$ is arginine, phenylalanine, N-nitroarginine, β-cycloarginine, γ-hydroxyarginine, N-amidinocitruline 2-amino-4-guanidinobutanoic acid, lysine, ornithine, tyrosine or tryptophan;

$AA_{10}$ is leucine, isoleucine, methionine or valine;

$AA_{11}$ is serine, threonine or alanine;

$AA_{12}$ is histidine, serine, threonine, cysteine, lysine or ornithine;

$AA_{13}$ is arginine, N-nitroarginine, β-cycloarginine, γ-hydroxyarginine, N-amidinocitruline or 2-amino-4-guanidinobutanoic acid;

$AA_{14}$ is proline, leucine, valine, isoleucine or methionine;

$AA_{15}$ is lysine, glutamine, histidine, ornithine, asparagine, arginine, N-nitroarginine, βcycloarginine, γ-hydroxyarginine, N-amidinocitruline or 2-amino-4-guanidinobutanoic acid;

$AA_{16}$ is threonine, aspartic acid, serine, glutamic acid or a substituted or unsubstituted aliphatic or aryl ester of glutamic acid or aspartic acid;

$AA_{17}$ is glycine, leucine, alanine, valine, isoleucine or methionine;

$AA_{18}$ is phenylalanine, tyrosine or tryptophan;

$AA_{19}$ is isoleucine, serine, valine, leucine, methionine, cysteine or threonine;

$AA_{20}$ is arginine, isoleucine, ornithine, lysine, N-nitroarginine, β-cycloarginine, γ-hydroxyarginine, N-amidinocitruline, 2-amino-4-guanidinobutanoic acid, leucine, valine or methionine;

$AA_{21}$ is methionine, isoleucine, leucine or valine;

$AA_{22}$ valine, arginine, leucine, isoleucine, methionine, ornithine, lysine, N-nitroarginine, β-cycloarginine, γ-hydroxyarginine, N-amidinocitruline or 2-amino-4-guanidinobutanoic acid;

$AA_{23}$ methionine, arginine, leucine, isoleucine, valine, ornithine, lysine, N-nitroarginine, β-cycloarginine, γ-hydroxyarginine, N-amidinocitruline or 2-amino-4-guanidinobutanoic acid;

$AA_{24}$ is phenylalanine, alanine, tyrosine, tryptophan or glycine;

$AA_{25}$ is aspartic acid, asparagine, glutamic acid, glutamine or a substituted or unsubstituted aliphatic or aryl ester of glutamic acid or aspartic acid;

$AA_{26}$ is glycine, arginine, alanine, ornithine, lysine, N-nitroarginine, β-cycloarginine, γ-hydroxyarginine, N-amidinocitruline or 2-amino-4-guanidinobutanoic acid;

$AA_{27}$ is lysine, alanine, arginine, glycine, serine, ornithine, arginine, N-nitroarginine, β-cycloarginine, γ-hydroxyarginine, N-amidinocitruline or 2-amino-4-guanidinobutanoic acid; and $AA_{28}$ is lysine, alanine, arginine, glycine, serine, ornithine, arginine, N-nitroarginine, β-cycloarginine, γ-hydroxyarginine, N-amidinocitruline or 2-amino-4-guanidinobutanoic acid, wherein the peptide has angiogenic activity, with the proviso that the peptide is not represented by SEQ ID NO.: 1 or a subsequence thereof.

2. The peptide of claim 1 wherein the peptide has an amino acid sequence comprising a subsequence of SEQ ID NO.: 1 and a subsequence of SEQ ID NO.: 2, wherein each subsequence has from five to fifteen amino acid residues.

3. The peptide of claim 1 wherein the peptide has an amino acid sequence consisting of a subsequence of SEQ ID NO.: 1 and a subsequence of SEQ ID NO.: 2, wherein each subsequence has from five to fifteen amino acid residues.

4. The peptide of claim 3 wherein the subsequence of SEQ ID NO.: 1 and the subsequence of SEQ ID NO.: 2 each have at least nine amino acid residues.

5. The peptide of claim 1 wherein the peptide is represented by SEQ ID NO.: 3, SEQ ID NO.: 4 or SEQ ID NOS. 9–12.

6. A peptide derivative of a peptide represented by SEQ ID NO.: 3, SEQ ID NO.: 4 or SEQ ID NOS. 9–12, wherein said peptide derivative has angiogenic activity.

7. The peptide derivative of claim 6 wherein the peptide derivative has between about ten and about twenty-eight amino acid residues or amino acid residue analogs.

8. The peptide derivative of claim 7 wherein the N-terminus is substituted with an amine protecting group and/or the C-terminus is substituted with a carboxylic acid protecting group.

9. The peptide derivative of claim 7 wherein the peptide derivative has an amino acid sequence corresponding to a subsequence of SEQ ID NO.: 3, SEQ ID NO.: 4 or SEQ ID NOS. 9–12 having from ten to fifteen amino acid residues.

10. The peptide derivative of claim 7 wherein the peptide derivative has an amino acid sequence corresponding to a subsequence of SEQ ID NO.: 3, SEQ ID NO.: 4 or SEQ ID NOS. 9–12 having from about ten to about fifteen amino acid residues, wherein one, two or three amino acid residues in the sequence of the peptide derivative can differ from the amino acid residue(s) in the corresponding position(s) of the subsequence.

11. The peptide derivative of claim 7 wherein the peptide derivative has an amino acid sequence corresponding to a subsequence of SEQ ID NO.: 3, or a subsequence of SEQ ID NO.: 4 or SEQ ID NOS. 9–12, said subsequence having from sixteen to twenty-eight amino acid residues.

12. The peptide derivative of claim 7 wherein the peptide derivative has an amino acid sequence corresponding to a subsequence of SEQ ID NO.: 3 or a subsequence of SEQ ID NO.: 4 or SEQ ID NOS. 9–12, said subsequence having from about sixteen to about twenty-eight amino acid residues, wherein one, two, three or four amino acid residues in the sequence of the peptide derivative can differ from the amino acid residue(s) in the corresponding position(s) of the subsequence.

13. The peptide derivative of claim 7 wherein the peptide derivative is represented by SEQ ID NO.: 3, SEQ ID NO.: 4 or SEQ ID NOS. 9–12.

\* \* \* \* \*

UNITED STATES PATENT AND TRADEMARK OFFICE
CERTIFICATE OF CORRECTION

PATENT NO. : 6,121,236
DATED : September 19, 2000
INVENTOR(S) : Shmuel A. Ben-Sasson It is certified that error appears in the above-identified patent and that said Letters Patent is hereby corrected as shown below:

Claim 1, column 31, line 63, insert a "," after N-amidinocitruline
Claim 1, column 32, line 46, insert a "-" after β

Signed and Sealed this

Fifteenth Day of May, 2001

NICHOLAS P. GODICI

*Attesting Officer*   Acting Director of the United States Patent and Trademark Office

UNITED STATES PATENT AND TRADEMARK OFFICE
CERTIFICATE OF CORRECTION

PATENT NO.    : 6,121,236
DATED         : September 19, 2000
INVENTOR(S)   : Shmuel A. Ben-Sasson It is certified that error appears in the above-identified patent and that said Letters Patent is hereby corrected as shown below:

<u>Title page,</u>
Item [73], Assignee, after "Children's Medical Center Corporation, Boston, MA (US)," add:
-- Yissum Research Development Company of the Hebrew University of Jerusalem, Jerusalem, Israel --

Signed and Sealed this

Twentieth Day of May, 2003

JAMES E. ROGAN
*Director of the United States Patent and Trademark Office*

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 35 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:1:

Arg His Ile Gly Trp Lys Asp Phe Thr Ala Tyr Arg Trp Arg Leu Ser

```
                 1               5              10              15
His Arg Pro Lys Thr Gly Phe Ile Arg Val Val Met Tyr Glu Gly Lys
                      20              25              30
Lys Ile Met
         35

(2) INFORMATION FOR SEQ ID NO:2:

(i) SEQUENCE CHARACTERISTICS:
        (A) LENGTH: 35 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:2:

Gln Ala Arg Ala Val Gly Leu Ala Gly Thr Phe Arg Ala Phe Leu Ser
 1               5              10              15
Ser Arg Leu Gln Asp Leu Tyr Ser Ile Val Arg Arg Ala Asp Arg Ala
                 20              25              30
Ala Val Trp
         35

(2) INFORMATION FOR SEQ ID NO:3:

(i) SEQUENCE CHARACTERISTICS:
        (A) LENGTH: 22 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= modified aa
            /note= "N-Acetyl Threonine"

(xi) SEQUENCE DESCRIPTION: SEQ ID NO:3:

Thr Phe Arg Ala Phe Leu Ser Ser Arg Leu Gln Thr Gly Phe Ile Arg
 1               5              10              15
Val Val Met Tyr Glu Gly
                 20

(2) INFORMATION FOR SEQ ID NO:4:

(i) SEQUENCE CHARACTERISTICS:
        (A) LENGTH: 22 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= modified aa
            /note= "N-Acetyl Alanine"

(xi) SEQUENCE DESCRIPTION: SEQ ID NO:4:

Ala Tyr Arg Trp Arg Leu Ser His Arg Pro Lys Asp Leu Tyr Ser Ile
 1               5              10              15
Val Arg Arg Ala Asp Gly
                 20
```

(2) INFORMATION FOR SEQ ID NO:5:

(i) SEQUENCE CHARACTERISTICS:
        (A) LENGTH: 35 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

```
Arg Asn Val Gly Trp Lys Asp Lys Val Ser Tyr Arg Trp Phe Leu Gln
 1               5                  10                  15

His Arg Pro Gln Val Gly Tyr Ile Arg Val Arg Phe Tyr Glu Gly Ser
            20                  25                  30

Glu Leu Val
        35
```

(2) INFORMATION FOR SEQ ID NO:6:

(i) SEQUENCE CHARACTERISTICS:
        (A) LENGTH: 35 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

```
Ile Ser Lys Thr Met Ser Gly Leu Glu Cys Gln Ala Trp Asp Ser Gln
 1               5                  10                  15

Ser Pro His Ala His Gly Tyr Ile Pro Ser Lys Phe Pro Asn Lys Asn
            20                  25                  30

Ile Lys Lys
        35
```

(2) INFORMATION FOR SEQ ID NO:7:

(i) SEQUENCE CHARACTERISTICS:
        (A) LENGTH: 22 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= modified aa
            /note= "N-Acetyl-Threonine"

(xi) SEQUENCE DESCRIPTION: SEQ ID NO:7:

```
Thr Phe Arg Ala Phe Leu Ser Ser Arg Leu Gln Asp Leu Tyr Ser Ile
 1               5                  10                  15

Val Arg Arg Ala Asp Gly
            20
```

(2) INFORMATION FOR SEQ ID NO:8:

(i) SEQUENCE CHARACTERISTICS:
        (A) LENGTH: 22 amino acids
        (B) TYPE: amino acid
        (C) STRANDEDNESS:
        (D) TOPOLOGY: linear

```
        (ii) MOLECULE TYPE: peptide (ix) FEATURE:
             (A) NAME/KEY: Modified-site
             (B) LOCATION: 1
             (D) OTHER INFORMATION: /label= modified aa
                 /note= "N-Acetyl-Alanine"

(xi) SEQUENCE DESCRIPTION: SEQ ID NO:8:

Ala Tyr Arg Trp Arg Leu Ser His Arg Pro Lys Thr Gly Phe Ile Arg
1               5                   10                  15

Val Val Met Tyr Glu Gly
            20

(2) INFORMATION FOR SEQ ID NO:9:

(i) SEQUENCE CHARACTERISTICS:
            (A) LENGTH: 23 amino acids
            (B) TYPE: amino acid
            (C) STRANDEDNESS:
            (D) TOPOLOGY: linear (ii) MOLECULE TYPE: peptide (ix) FEATURE:
             (A) NAME/KEY: Modified-site
             (B) LOCATION: 1
             (D) OTHER INFORMATION: /label= modified aa
                 /note= "N-Acetyl-Threonine"

(xi) SEQUENCE DESCRIPTION: SEQ ID NO:9:

Thr Ala Tyr Arg Trp Arg Leu Ser His Arg Pro Lys Asp Leu Tyr Ser
1               5                   10                  15

Ile Val Arg Arg Ala Asp Arg
            20

(2) INFORMATION FOR SEQ ID NO:10:

(i) SEQUENCE CHARACTERISTICS:
            (A) LENGTH: 22 amino acids
            (B) TYPE: amino acid
            (C) STRANDEDNESS:
            (D) TOPOLOGY: linear (ii) MOLECULE TYPE: peptide (ix) FEATURE:
             (A) NAME/KEY: Modified-site
             (B) LOCATION: 1
             (D) OTHER INFORMATION: /label= modified aa
                 /note= "N-Acetyl-Alanine"

(xi) SEQUENCE DESCRIPTION: SEQ ID NO:10:

Ala Tyr Arg Trp Arg Leu Ser His Arg Pro Lys Asp Leu Tyr Ser Ile
1               5                   10                  15

Val Arg Arg Ala Asp Arg
            20

(2) INFORMATION FOR SEQ ID NO:11:

(i) SEQUENCE CHARACTERISTICS:
            (A) LENGTH: 20 amino acids
            (B) TYPE: amino acid
            (C) STRANDEDNESS:
            (D) TOPOLOGY: linear (ii) MOLECULE TYPE: peptide (ix) FEATURE:
             (A) NAME/KEY: Modified-site
```

```
            (B) LOCATION: 1
            (D) OTHER INFORMATION: /label= modified aa
                /note= "Alpha N-Acetyl Arginine"

(xi) SEQUENCE DESCRIPTION: SEQ ID NO:11:

Arg Trp Arg Leu Ser His Arg Pro Lys Asp Leu Tyr Ser Ile Val Arg
1               5                   10                  15

Arg Ala Asp Arg
            20

(2) INFORMATION FOR SEQ ID NO:12:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= modified aa
            /note= "Alpha N-Acetyl Lysine"

(xi) SEQUENCE DESCRIPTION: SEQ ID NO:12:

Lys Asp Phe Thr Ala Tyr Arg Trp Arg Leu Ser His Arg Pro Lys Asp
1               5                   10                  15

Leu Tyr Ser Ile Val Arg Arg Ala Asp Arg
            20                  25

(2) INFORMATION FOR SEQ ID NO:13:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

Gly Gly Gly Gly Ser Gly Gly Gly Gly Ser Gly Gly Gly Gly Ser
1               5                   10                  15

(2) INFORMATION FOR SEQ ID NO:14:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:14:

Gly Gly Gly Gly Ser Gly Gly Gly Gly Ser Gly Gly Gly Gly Ser Gly
1               5                   10                  15

Gly Gly Gly Ser
            20

(2) INFORMATION FOR SEQ ID NO:15:

(i) SEQUENCE CHARACTERISTICS:
        (A) LENGTH: 190 amino acids
        (B) TYPE: amino acid
        (C) STRANDEDNESS:
```

-continued (D) TOPOLOGY: linear (ii) MOLECULE TYPE: peptide (xi) SEQUENCE DESCRIPTION: SEQ ID NO:15:

```
Lys Asp Phe Thr Ala Tyr Arg Trp Arg Leu Ser His Arg Pro Lys Asp
1               5                   10                  15

Leu Tyr Ser Ile Val Arg Arg Ala Asp Arg Gly Gly Gly Gly Ser Gly
            20                  25                  30

Gly Gly Gly Ser Gly Gly Gly Gly Ser Lys Asp Phe Thr Ala Tyr Arg
            35              40                  45

Trp Arg Leu Ser His Arg Pro Lys Asp Leu Tyr Ser Ile Val Arg Arg
        50                  55                  60

Ala Asp Arg Gly Gly Gly Gly Ser Gly Gly Gly Ser Gly Gly Gly
65              70                  75                  80

Gly Ser Lys Asp Phe Thr Ala Tyr Arg Trp Arg Leu Ser His Arg Pro
                85                  90                  95

Lys Asp Leu Tyr Ser Ile Val Arg Arg Ala Asp Arg Gly Gly Gly Gly
                100                 105                 110

Ser Gly Gly Gly Gly Ser Gly Gly Gly Gly Ser Lys Asp Phe Thr Ala
            115                 120                 125

Tyr Arg Trp Arg Leu Ser His Arg Pro Lys Asp Leu Tyr Ser Ile Val
        130                 135                 140

Arg Arg Ala Asp Arg Gly Gly Gly Gly Ser Gly Gly Gly Gly Ser Gly
145                 150                 155                 160

Gly Gly Ser Lys Asp Phe Thr Ala Tyr Arg Trp Arg Leu Ser His
                165                 170                 175

Arg Pro Lys Asp Leu Tyr Ser Ile Val Arg Arg Ala Asp Arg
                180                 185                 190
```